US006380204B1

(12) United States Patent
Chenard et al.

(10) Patent No.: US 6,380,204 B1
(45) Date of Patent: Apr. 30, 2002

(54) ATROPISOMERS OF 3-HETEROARYL-4(3H)-QUINAZOLINONES FOR THE TREATMENT OF NEURODEGENERATIVE AND CNS-TRAUMA RELATED CONDITIONS

(75) Inventors: Bertrand Leo Chenard; Keith Michael Devries, both of Waterford; Willard McKowan Welch, Jr., Mystic, all of CT (US)

(73) Assignee: Pfizer INC, New York, NY (US)

(*) Notice: Subject to any disclaimer, the term of this patent is extended or adjusted under 35 U.S.C. 154(b) by 0 days.

(21) Appl. No.: 09/380,114

(22) PCT Filed: Feb. 6, 1998

(86) PCT No.: PCT/IB98/00151

§ 371 Date: Jan. 13, 2000

§ 102(e) Date: Jan. 13, 2000

(87) PCT Pub. No.: WO98/38187

PCT Pub. Date: Sep. 3, 1998

(30) Foreign Application Priority Data

Feb. 28, 1997 (US) .......................................... 60038540

(51) Int. Cl.[7] ....................... C07D 401/04; A01N 43/54

(52) U.S. Cl. ....................... 514/259; 544/284; 544/290

(58) Field of Search ................................ 544/283, 287, 544/284, 290; 514/266, 259

(56) References Cited

U.S. PATENT DOCUMENTS 4,183,931 A 1/1980 Wolfe et al.

FOREIGN PATENT DOCUMENTS

| | | | |
|---|---|---|---|
| DE | 2114607 | | 2/1971 |
| EP | 0807633 | | 11/1997 |
| WO | WO 9213535 | * | 8/1992 |
| WO | 9213535 | | 8/1992 |
| WO | 9743276 | | 11/1997 |
| WO | WO 9743276 | * | 11/1997 |

OTHER PUBLICATIONS

A. Kumar, et al.; Synthesis and Hypotensive Activity of Trisubstituted Quinazolinones; Eur. Med. Chem. (1985); pp. 95–96.

Vijai K. Srivastava, et al.; Synthesis of Some Quinazolones; Indian J. Pharm. Sci.; (1986) vol. 48, No. 5; pp. 133–136.

Th. Jira, et al.; Zur Synthese und HPLC–Trennung atropisomer und zentral chiraler 3–Aryl–2–mercapto– und 3–Aryl–2–alkylthio–4(3H)–chinazolinonderivate an chiralen stationaren Phasen; Pharmazie, 51 (1996); pp. 273–279.

A.K. El–Ansary, et al.; Synthese of Some Quinazolone Derivatives Structurally Related to Certain Sedatives, Hypnotics and Anticonvulsant Agents; Pharmazie 34, (1979); pp. 753–756.

Th. Jira, et al.; Zur Synthese und HPLC–Trennung atropisomer und zentral chiraler 3–Aryl–2–mercapto– und 3–Aryl–2–alkylthio–4(3H)–chinazolinonderivate an chiralen stationaren Phasen; Pharmazie, 51 (1996); pp. 379–386.

B. Kenneth Koe, etal.; Enhancement of Benzodiazepine Binding by Methaqualone and Related Quinazolinones; Drug Development Research; (1986) pp. 255–268.

Lawrence D. Colebrook, et. al.; Hindered Internal Rotation About Aryl C–N Bonds in Aryl Substituted Heterocyclic Compounds: 3–Aryl–2–benzyl–4(3H)–quinaolinones; Can. J. Chem. vol. 53, (1975); 3431–3434.

A. Mannschreck, et al.; The Enantiomers of Methaqualone and their unequal Anticonvulsive Activity; Eur. J. Med. Chem.; (1984) pp. 381–383.

* cited by examiner

*Primary Examiner*—John M. Ford
(74) *Attorney, Agent, or Firm*—Peter C. Richardson; Paul H. Ginsburg; A. David Joran

(57) ABSTRACT

The present invention relates to novel atropisomers of 3-heteroaryl-4(3H)-quinazolinones of the formula Ia, and their pharmaceutically acceptable salts, and pharmaceutical compositions and methods of treating neurodegenerative and CNS-trauma related conditions.

13 Claims, No Drawings

ATROPISOMERS OF 3-HETEROARYL-4(3H)-QUINAZOLINONES FOR THE TREATMENT OF NEURODEGENERATIVE AND CNS-TRAUMA RELATED CONDITIONS

This is a national stage application under 35 USC §371 of PCT International Application No. PCT/IB98/00151, filed Feb. 6, 1998, which claims the benefit of Ser. No. 60/038,540, filed Feb. 28, 1997.

BACKGROUND OF THE INVENTION

The present invention relates to atropisomers of 3-heteroaryl-4(3H)-quinazolinones of the formula Ia, described below, and their pharmaceutically acceptable salts, and pharmaceutical compositions and methods of treating neurodegenerative and CNS-trauma related conditions.

Atropisomers are isomeric compounds that are chiral, i.e. each isomer is not superimposable on its mirror image and the isomers, once separated, rotate polarized light in equal amounts but opposite directions. Atropisomers are distinguished from enantiomers in that atropisomers do not possess a single asymmetric atom. Atropisomers are conformational isomers which occur when rotation about a single bond in the molecule is prevented or greatly slowed as a result of steric interactions with other parts of the molecule and the substituents at both ends of the single bond are unsymmetrical. A detailed account of atropisomers can be found in Jerry March, *Advanced Organic Chemistry*, 101–102 (4th ed. 1992) and in Oki, *Top. Stereochem.*, 14, 1–81 (1983).

The compounds of the invention provide the first evidence that atropisomers of quinazolinones are separable and that the separated isomers possess differential AMPA receptor antagonist activity. (AMPA receptors are a subspecies of glutamate receptors, identified by their ability to bind α-amino-3-hydroxy-5-methyl-4-isoxazolepropionic acid (AMPA), that are post-synaptic neurotransmitter receptors for excitatory amino acids.) Colebrook et al., *Can. J. Chem.*, 53, 3431–4, (1975) observed hindered rotation about aryl C═N bonds in quinazolinones but did not separate or suggest that the rotational isomers could be separated. U.S. patent application Ser. No. 60/017,738 filed May 15,1996 and entitled "Novel 2,3-Disubstituted-4-(3H)-Quinazolinones" and U.S. patent application Ser. No. 60/017,737 filed May 15, 1996 and entitled "Novel 2,3-Disubstituted-(5,6)-Heteroarylfused-Pyrimidin-4-ones," both applications herein incorporated by reference in there entirety, refer to racemic quinazolinones and pyrimidinones. Suprisingly, the inventors of the present invention have discovered that one quinazolinone isomer, defined by the spatial positions of the substituents arising out of steric interactions, possesses all of the AMPA receptor antagonist activity.

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges,and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinosoitide hydrolysis in the postsynaptic cell. Both types of receptors appear not only to mediate normal synaptic transmission along excitatory pathways, but also participate in the modification of synaptic connection during development and changes in the efficiency of synaptic transmission throughout life. Schoepp, Bockaert, and Sladeczek. *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, ocular damage and retinopathy, and idiopathic and drug-induced Parkinson's Disease. Other neurological conditions, that are caused by glutamate dysfunction, require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic pain, convulsions, retinal neuropathy, tinnitus and tardive dyskinesia. The use of a neuroprotective agent, such as an AMPA receptor antagonist, is believed to be useful in treating these disorders and/or reducing the amount of neurological damage associated with these disorders. The excitatory amino acid receptor (EAA) antagonists are also useful as analgesic agents.

Several studies have shown that AMPA receptor antagonists are neuroprotective in focal and global ischemia models. The competitive AMPA receptor antagonist NBQX (2,3-dihydroxy-6-nitro-7-sulfamoylbenzo[f-]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonists GKYI 52466 has been shown to be an effective neuroprotective agent in rat global ischemia models. LaPeillet et al., *Brain Research*, 571, 115 (1992).

These studies strongly suggest that the delayed neuronal degeneration in brain ischemia involves glutamate excitotoxicity mediated at least in part by AMPA receptor activation. Thus, AMPA receptor antagonists may prove useful as neuroprotective agents and improve the neurological outcome of cerebral ischemia in humans.

SUMMARY OF THE INVENTION

The present invention relates to an atropisomer of the formula

Ia

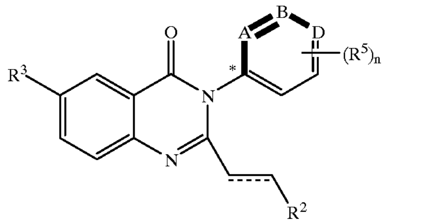

wherein each of "A, B and D" is nitrogen or —CH—, with the proviso that only one of "A", "B" and "D" can be nitrogen; wherein n is an integer from one to four, preferably one to or two, and wherein each $R^5$ is a substituent on any carbon atom of the "A, B, D" ring capable of supporting an additional bond, with the proviso that one $R^5$ must be attached to a carbon atom ortho to the asterisked carbon of the ring; wherein each $R^5$ may be independently selected from the group consisting of $(C_1-C_6)$alkyl, halogen, trifluoromethyl, amino-$(CH_2)_m$—, $(C_1-C_6)$alkylamino-$(CH_2)_m$—, di$(C_1-C_6)$alkyl-amino-$(CH_2)_m$—, $(C_1-C_6)$alkoxy, hydroxy$(C_1-C_6)$alkyl-, $(C_1-C_6)$alkyl-O—$(C_1-C_6)$alkyl-, —CN, hydroxy-$(CH_2)_m$—, $(C_1-C_6)$alkyl-(O=C)—O—$(C_1-C_6)$alkyl-, $(C_1-C_6)$alkyl-O—(C=O)—O—$(C_1-C_6)$alkyl, $(C_1-C_6)$alkyl-(O=C)—O—, H—(C=O)—$(CH_2)_m$—, $(C_1-C_6)$alkyl-(C=O)—$(CH_2)_m$—, HO—(C=O)—, $(C_1-C_6)$alkyl-O—(C=O)—$(CH_2)_m$—, $NH_2$—(C=O)—$(CH_2)_m$—, $(C_1-C_6)$alkyl-NH—(C=O)—$(CH_2)_m$—, and di$(C_1-C_6)$alkyl-N—(C=O)—$(CH_2)_m$—; and wherein m is an integer from zero to four;

$R^2$ is a phenyl group of the formula $Ph^2$ or a five or six membered heterocycle;

wherein said 6-membered heterocycle has the formula

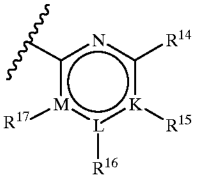

wherein "N" is nitrogen; wherein said ring positions "K", "L" and "M" may be independently selected from carbon and nitrogen, with the proviso that i) only one of "K", "L" and "M" can be nitrogen and ii) when "K", "L" or "M" is nitrogen, then its respective $R^{15}$, $R^{16}$ or $R^{17}$ is absent;

wherein said five membered heterocycle has the formula

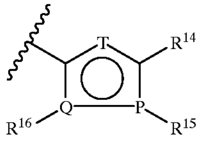

wherein said "T" is —CH—, N, NH, O or S; wherein said ring positions "P" and "Q" may be independently selected from carbon, nitrogen, oxygen and sulfur; with the proviso that only one of "P," "Q" or "T" can be oxygen or sulfur and at least one of "P", "Q" or "T" must be a heteroatom;

wherein said $Ph^2$ is a group of the formula

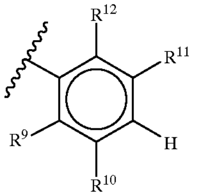

$R^3$ is hydrogen, halo, —CN, —$NO_2$, $CF_3$, $(C_1-C_6)$alkyl or $(C_1-C_6)$alkoxy;

$R^9$ is hydrogen, halo, $CF_3$, $(C_1-C_6)$alkyl optionally substituted with one to three halogen atoms, $(C_1-C_6)$alkoxy optionally substituted with one to three halogen atoms, $(C_1-C_6)$alkylthiol, amino-$(CH_2)_s$—, $(C_1-C_6)$alkyl-NH—$(CH_2)_s$—, di$(C_1-C_6)$alkyl-N—$(CH_2)_s$—, $(C_3-C_7)$cycloalkyl-NH—$(CH_2)_s$—, $H_2N$—(C=O)—$(CH_2)_s$—, $(C_1-C_6)$alkyl-HN—(C=O)—$(CH_2)_s$—, di$(C_1-C_6)$alkyl-N—(C=O)—$(CH_2)_s$—, $(C_3-C_7)$cycloalkyl-NH—(C=O)—$(CH_2)_s$—, $R^{13}$O—$(CH_2)_s$—, $R^{13}$O—(C=O)—$(CH_2)_s$—, H(O=C)—NH—$(CH_2)_s$—, $(C_1-C_6)$alkyl-(O=C)—NH—$(CH_2)_s$—,

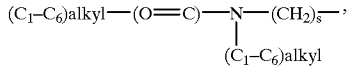

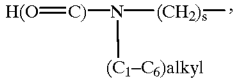

H—(C=O)—$(CH_2)_s$—, $(C_1-C_6)$alkyl-(C=O)—, hydroxy, hydroxy-$(C_1-C_6)$alkyl-, $(C_1-C_6)$alkyl-O—$(C_1-C_6)$alkyl-, or —CN;

$R^{10}$ is hydrogen or halo;

$R^{11}$ and $R^{14}$ are selected, independently, from hydrogen, halo, $CF_3$, $(C_1-C_6)$alkyl optionally substituted with one to three halogen atoms, $(C_1-C_6)$alkoxy optionally substituted with one to three halogen atoms, $(C_1-C_6)$alkylthiol, amino-$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, amino-$C_1-C_6$)alkyl-NH—$(CH_2)_p$—, $(C_1-C_6)$alkyl-NH—$(C_1-C_6)$alkyl-NH—$(CH_2)_p$—, di$(C_1-C_6)$alkyl-N—$(C_1-(C_6)$alkyl-NH—$(CH_2)_p$—,

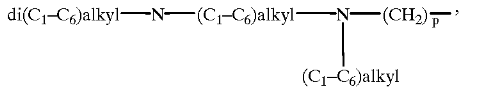

$H_2N$—(C=O)—$(CH_2)_p$—, $(C_1$–$C_6)$alkyl-HN—(C=O)—$(CH_2)_p$—, di$(C_1$–$C_6)$alkyl-N—(C=O)—$(CH_2)_p$, $(C_3$–$C_7)$cycloalkyl-NH—(C=O)—$(CH_2)_p$—, $R^{13}$O—$(CH_2)_p$—, $R^{13}$O—(C=O)—$(CH_2)_p$—, H(O=C)—O—, H(O=C)—O—$(C_1$–$C_6)$alkyl-, H(O=C)—NH—$(CH_2)_p$—, $(C_1$–$C_6)$alkyl-(O=C)—NH—$(CH_2)_p$—, —CHO, H—(C=O)—$(CH_2)_p$—, $(C_1$–$C_6)$ alkyl-(C=O)—$(CH_2)_p$—,

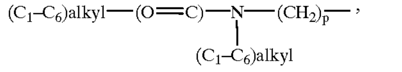

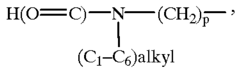

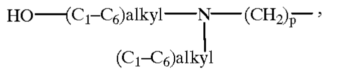

$(C_1$–$C_6)$alkyl-(C=O)—O—$(CH_2)_p$—, amino-$(C_1$–$C_6)$ alkyl-(C=O)—O—$(CH_2)_p$—, $(C_1$–$C_6)$alkyl-NH—$(C_1$–$C_6)$alkyl-(C=O)—O—$(CH_2)_p$—, di$(C_1$–$C_6)$ alkyl-N—$(C_1$–$C_6)$alkyl-(C=O)—O—$(CH_2)_p$—, amino-$(C_1$–$C_6)$alkyl-O—(C=O)—$(CH_2)_p$—, $(C_1$–$C_6)$ alkyl-NH—$(C_1$–$C_6)$alkyl-O—(C=O)—$(CH_2)_p$—, di$(C_1$–$C_6)$alkyl-N—$(C_1$–$C_6)$alkyl-O—(C=O)—$(CH_2)_p$—, hydroxy, hydroxy-$(C_1$–$C_6)$alkyl-, hydroxy-$(C_1$–$C_6)$alkyl-NH—$(CH_2)_p$—, $(C_1$–$C_6)$alkyl-O—$(C_1$–$C_6)$alkyl-, —CN, piperidine-$(CH_2)_p$—, pyrrolidine-$(CH_2)_p$—, and 3-pyrroline-$(CH_2)_p$—, wherein said piperidine, pyrrolidine and 3-pyrroline moieties of said piperidine-$(CH_2)_p$—, pyrrolidine-$(CH_2)_p$— and 3-pyrroline-$(CH_2)_p$— groups may optionally be substituted on any of the ring carbon atoms capable of supporting an additional bond, preferably zero to two substituents, with a substituent independently selected from halo, $CF_3$, $(C_1$–$C_6)$alkyl optionally substituted with one to three halogen atoms, $(C_1$–$C_6)$alkoxy optionally substituted with one to three halogen atoms, $(C_1$–$C_6)$alkylthiol, amino-$(CH_2)_p$—, $(C_1$–$C_6)$alkyl-NH—$(CH_2)_p$—, di$(C_1$–$C_6)$alkyl-N—$(CH_2)_p$—, $(C_3$–$C_7)$cycloalkyl-NH—$(CH_2)_p$—, amino-$(C_1$–$C_6)$alkyl-NH—$(CH_2)_p$—, $(C_1$–$C_6)$akyl-NH—$(C_1$–$C_6)$alkyl-NH—$(CH_2)_p$—, di$(C_1$–$C_6)$alkyl-N—$(C_1$–$C_6)$alkyl-, NH—$(CH_2)_p$—, $(C_1$—$C_6)$alkyl-O—$(C_1$–$C_6)$ aklyl-,

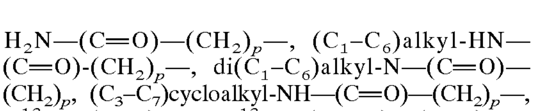

$H_2N$—(C=O)—$(CH_2)_p$—, $(C_1$–$C_6)$alkyl-HN—(C=O)-$(CH_2)_p$—, di$(C_1$–$C_6)$alkyl-N—(C=O)—$(CH_2)_p$, $(C_3$–$C_7)$cycloalkyl-NH—(C=O)—$(CH_2)_p$—, $R^{13}$O—$(CH_2)_p$—, $R^{13}$O—(C=O)—$(CH_2)_p$—, H(O=C)—O—, H(O=C)—O—$(C_1$–$C_6)$alkyl-, H(O=C)—NH—$(CH_2)_p$—, $(C_1$–$C_6)$alkyl-(O=C)—NH—$(CH_2)_p$—, —CHO, H—(C=O)—$(CH_2)_p$—, $(C_1$–$C_6)$alkyl-(C=O)—,

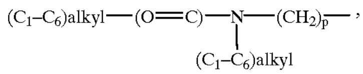

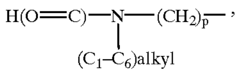

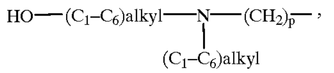

$(C_1$–$C_6)$alkyl-(C=O)—O—NH—$(CH_2)_p$—, amino-$(C_1$–$C_6)$alkyl-(C=O)—O—$(CH_2)_p$—, $(C_1$–$C_6)$alkyl-NH—$(C_1$–$C_6)$alkyl-(C=O)—O—$(CH_2)_p$—, di$(C_1$–$C_6)$alkyl-N—$(C_1$–$C_6)$alkyl-(C=O)—O—$(CH_2)_p$—, hydroxy, hydroxy-$(C_1$–$C_6)$alkyl-, hydroxy-$(C_1$–$C_6)$alkyl-NH—$(CH_2)_p$—, and —CN;

$R^{12}$ is hydrogen, —CN or halo;

$R^{13}$ is hydrogen, $(C_1$–$C_6)$alkyl, $(C_1$–$C_6)$alkyl-(C=O)—, $(C_1$–$C_6)$alkyl-O—(C=O)—, $(C_1$–$C_6)$alkyl-NH $(C_1$–$C_6)$alkyl, di$(C_1$–$C_6)$-alkyl-N—$(C_1$–$C_6)$alkyl-, $(C_1$–$C_6)$alkyl-NH—(C=O)—, or di$(C_1$–$C_6)$alkyl-N—(C=O)—;

$R^{15}$ is hydrogen, —CN, $(C_1$–$C_6)$alkyl, halo, $CF_3$, —CHO or $(C_1$–$C_6)$alkoxy;

$R^{16}$ is hydrogen, —CN, $(C_1$–$C_6)$alkyl, halo, $CF_3$, —CHO or $(C_1$–$C_6)$alkoxy;

$R^{17}$ is hydrogen, —CN, $(C_1$–$C_6)$alkyl, amino-$(C_1$–$C_6)$ alkyl-, $(C_1$–$C_6)$alkyl-NH—$(C_1$–$C_6)$alkyl-, di$(C_1$–$C_6)$ alkyl-N—$(C_1$–$C_6)$alkyl-, halo, $CF_3$, —CHO or $(C_1$–$C_6)$ alkoxy;

each p is independently an integer from zero to 4;

s is an integer from zero to 4;

wherein the dashed bond represented an optional double bond;

and the pharmaceutically acceptable salts of such compounds.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

Preferred compounds of formula I are those wherein $R^3$ is hydrogen, halo or $(C_1$–$C_6)$alkyl.

Other preferred compounds of formula Ia are those wherein "B" is nitrogen and "A" and "D" are carbon and $R^5$ is hydrogen, halo, —CN, $CF_3$, or $(C_1-C_6)$alkyl, preferably $R^5$ is chloro or methyl, more preferably $R^5$ is a substituent ortho to the asterisked carbon.

Preferred compounds of formula Ia wherein $R^2$ is $Ph^2$ are those wherein $R^9$ is fluoro, chloro, —CN or hydroxy; or $R^{11}$ is —CHO, chloro, fluoro, methyl, $(C_1-C_6)$alkyl-NH—$(CH_2)_p$—, di$(C_1-C_6)$alkyl-N—$(CH_2)_p$—, pyrrolidine-$(CH_2)_p$— or cyano. Most preferred compounds of formula Ia wherein $R^2$ is $Ph^2$ are those wherein $R^9$ is fluoro or —CN; or $R^{11}$ is methyl, $(C_1-C_6)$alkyl-NH—$(CH_2)_p$—, di$(C_1-C_6)$alkyl-N—$(CH_2)_p$—, or cyano.

Preferred compounds of formula Ia wherein $R^2$ is heteroaryl are those wherein said heteroaryl is either an optionally substituted six-membered heterocycle wherein "K", "L" and "M" are carbon (i.e. pyridin-2-yl), or "K" and "L" are carbon and "M" is nitrogen (i.e. pyrimidin-2-yl), or said heteroaryl is an optionally substituted five membered heterocycle wherein "T" is nitrogen, "P" is sulfur and "Q" is carbon (i.e. 1,3-thiazol-4-yl), or "T" is nitrogen or sulfur, "Q" is nitrogen or sulfur and "P" is carbon (i.e. 1,3-thiazol-2-yl) or "T" is oxygen and "P" and "Q" are each carbon (i.e. fur-2-yl).

Preferred compounds of formula Ia wherein $R^2$is an optionally substituted six-membered heterocycle wherein "K", "L" and "M" are carbon (i.e. pyridin-2-yl) are those wherein $R^{14}$ is hydrogen, —CHO, chloro, fluoro, methyl, $(C_1-C_6)$alkyl-NH—$(CH_2)_p$—, di$(C_1-C_6)$alkyl-N—$(CH_2)_p$—, pyrrolidine-$(CH_2)_p$— or cyano; $R^{17}$ is hydrogen, —CHO, chloro, fluoro, methyl, $(C_1-C_6)$alkyl-NH—$(C_1-C_6)$alkyl, di$(C_1-C_6)$alkyl-N—$(C_1-C_6)$alkyl, or cyano; or $R^{15}$ or $R^{16}$ are independently hydrogen, —CHO, chloro, fluoro, methyl or cyano. Most preferred compounds of formula Ia wherein $R^2$ is an optionally substituted six-membered heterocycle wherein "K", "L" and "M" are carbon (i.e. pyridin-2-yl) are those wherein $R^{14}$ is hydrogen, —CHO, methyl, $(C_1-C_6)$alkyl-NH—$(CH_2)_p$—, di$(C_1-C_6)$alkyl-N—$(CH_2)_p$—, or cyano.

Preferred compounds of formula Ia wherein $R^2$ is an optionally substituted five-membered heterocycle wherein "T" is nitrogen, "P" is sulfur and "Q" is carbon (i.e. 1,3-thiazol-4-yl) are those wherein $R^{14}$, $R^{15}$ or $R^{16}$ i.e., are each independently hydrogen, chloro, fluoro, methyl or cyano.

Preferred compounds of formula Ia wherein $R^2$ is an optionally substituted five-membered heterocycle wherein "T" is nitrogen or sulfur, "Q" is sulfur or nitrogen and "P" is carbon (i.e. 1,3-thiazol-2-yl) are those wherein $R^{14}$ or $R^{15}$ are independently hydrogen, chloro, fluoro, methyl or cyano.

Examples of specific preferred compounds of formula Ia include:

(S)-6-fluoro-2-[2-(2-fluoro-phenyl)-vinyl]-3-(2-methyl-pyridin-3-yl)-3H-quinazolin-4-one;

(S)-2-{2-[6-fluoro-3-(2-methyl-pyridin-3-yl)-4-oxo-3,4-dihydro-quinazolin-2-yl]-vinyl}-benzonitrile;

(S)-2-{2-[6-fluoro-3-(2-methylpyridin-3-yl)-4-oxo-3,4-dihydroquinazolin-2-yl]-vinyl}-benzonitrile;

(S)-2-{2-[3-(2-chloro-pyridin-3-yl) -6-fluoro-4-oxo-3,4-dihydroquinazolin-2-yl]-vinyl}-benzonitrile;

(S)-2-{2-[6-fluoro-3-(2-methyl-pyridin-3-yl)-4-oxo-3,4-dihydro-quinazolin-2-yl]-vinyl}-4-methyl-benzonitrile;

(S)-2-{2-[3-(2-methyl-pyridin-3-yl)-4-oxo-3,4-dihydro-quinazolin-2-yl]-vinyl}-benzonitrile;

(S)-6-fluoro-3-(2-methyl-pyridin-3-yl)-2-[2-(2-thiazol-4-yl)-vinyl]-3H-quinazolin-4-one;

(S)-6-fluoro-3-(2-methyl-pyridin-3-yl)-2-[2-(2-methyl-thiazol-4-yl)-vinyl]-3H-quinazolin-4-one;

(S)-6-fluoro-3-(2-methyl-pyridin-3-yl)-2-[2-(4-methyl-thiazol-2-yl)-vinyl]-3H-quinazolin-4-one;

(S)-2-[2-(5-diethylaminomethyl-2-fluoro-phenyl)-vinyl]-6-fluoro-3-(2-methyl-pyridin-3-yl)-3H-quinazolin-4-one; and (S)-6-fluoro-2-[2-(2-fluoro-5-pyrrolidin-1-ylmethyl-phenyl)-vinyl]-3-(2-methyl-pyridin-3-yl)-3H-quinazolin-4-one.

Other compounds of the invention include:

(S)-3-(2-chloro-pyridin-3-yl)-2-[2-(2-fluoro-phenyl)-vinyl]-3H-quinazolin-4-one;

(S)-3-(2-chloro-pyridin-3-yl)-6-fluoro-2-[2-(6-methyl-phenyl-2-yl)-vinyl]-3H-quinazolin-4-one;

(S)-3-(2-chloro-pyridin-3-yl)-6-fluoro-2-[2-(fluoro-phenyl)-vinyl]-3H-quinazolin-4-one;

(S)-6-chloro-2-[2-(2-fluoro-phenyl)-vinyl]-3-(2-methyl-pyridin-3-yl)-3H-quinazolin-4-one;

(S)-6-chloro-2-[2-(2-fluoro-phenyl)-vinyl]-3-(3methyl-1-oxy-pyridin-4-yl)-3H-quinazolin-4-one;

(S)-3-{2-[3-(2-chloro-pyridin-3-yl)-6-fluoro-4-oxo-3,4-dihydro-quinazolin-2-yl]-vinyl}-benzaldehyde;

(S)-3-{2-[3-(2-chloro-pyridin-3-yl) -4-oxo-3,4-dihydro-quinazolin-2-yl]-vinyl}-benzaldehyde;

(S)-3-(2-chloro-pyridin-3-yl)-6-fluoro-2-[2-(3-hydroxymethyl-phenyl)-vinyl]-3H-quinazolin-4-one;

(S)-3-(2-chloro-pyridin-3-yl)-2-{2-[3(1,4-dioxa-8-aza-spiro[4.5]dec-8-ylmethyl)-phenyl]-vinyl}-6-fluoro-3H-quinazolin-4-one;

(S)-3-(2-chloro-pyridin-3-yl)-6-fluoro-2-{2-[3-(4-pyrrolidin-1-yl-piperidin-1-ylmethyl)-phenyl]-vinyl}-3H-quinazolin-4-one;

(S)-2-{2-[3-(2-chloro-pyridin-3-yl-6-fluoro-4-oxo-3,4-dihydro-quinazolin-2-yl]-vinyl}-benzonitrile;

(S)-2-{2-[3-(2-chloro-pyridin-3-yl)-4-oxo-3,4-dihydro-quinazolin-2-yl]-vinyl}-benzonitrile;

(S)-2-[2-(2-fluoro-phenyl)-vinyl]-3-(2-methyl-pyridin-3-yl)-3H-quinazolin-4-one;

(S)-3-(2-chloro-pyridin-3-yl) -6-fluoro-2-[2-hydroxy-phenyl)-vinyl]-3H-quinazolin-4-one;

(S)-6-fluoro-3-(2-methyl-pyridin-3-yl)-2-[2-(2-methyl-thiazol-4-yl)-ethyl]-3H-quinazolin-4-one;

(S)-6-fluoro-3-(2-chloro-pyridin-3-yl)-2-[2-(2-dimethylamino-methylthiazo-4-yl)-vinyl]-3H-quinazolin-4-one;

(S)-2-[2-(5-Diethylaminomethyl-2-fluoro-phenyl)-vinyl]-6-fluoro-3-(4-methyl-pyridin-3-yl)-3H-quinazolin-4-one (S)-4-Diethylaminomethyl-2-(2-[6-fluoro-3-(4-methyl-pyridin-3-yl)-4-oxo-3,4-dihydro-quinazolin-2-yl]-vinyl}-benzonitrile (S)-2-[2-(5-Diethylaminomethyl-2-fluoro-phenyl)-vinyl]-6-fluoro-3-(3-methyl-pyrazin-2-yl)-3H-quinazolin-4-one (S)-6-fluoro-3-(2-methyl-pyridin-3-yl)-2-[2-(2-dimethylamino-methylthiazol-4-yl)-vinyl]-3H-quinazolin-4-one;

(S)-6-fluoro-3-(2-methyl-pyridin-3-yl)-2-[2-(2-methyl-oxazol-4-yl)-vinyl]-3H-quinazolin-4-one;

(S)-6-fluoro-3-(2-chloro-pyridin-3-yl)-2-[2-(2-thiazol-4-yl)-vinyl]-3H-quinazolin-4-one;

(S)-6-fluoro-3-(4-methyl-pyridin-3-yl)-2-[2-(4-methyl-thiazol-2-yl)-vinyl]-3H-quinazolin-4-one;

(S)-3-(2-chloro-pyridin-3-yl)-6-fluoro-2-[2-(2-hydroxy-phenyl)-vinyl]-3H-quinazolin-4-one; and (S)-6-fluoro-2-[2-(2-fluoro-5-pyrrolidin-1-ylmethyl-phenyl)-ethyl]-3-(2-methyl-pyridin-3-yl)-3H-quinazolin-4-one.

This invention also relates to a pharmaceutical composition for treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), idiopathic and drug induced Parkinson's Disease and brain edema, and muscular spasms, migraine headaches, urinary incontinence, psychosis, convulsions, chronic or acute pain, ocular damage, retinopathy, retinal neuropathy, tinnitus, anxiety, emesis and tardive dyskinesia, in a mammal, comprising an amount of a compound of formula Ia effective in treating or preventing such condition and a pharmaceutically acceptable carrier.

This invention also relates to a method of treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), idiopathic and drug induced Parkinson's Disease and brain edema, and muscular spasms, migraine headaches, urinary incontinence, psychosis, convulsions, chronic or acute pain, ocular damage, retinopathy, retinal neuropathy, tinnitus, anxiety, emesis and tardive dyskinesia, in a mammal, comprising administering to a mammal in need of such treatment or prevention an amount of a compound of formula Ia effective in treating or preventing such condition.

This invention also relates to a pharmaceutical composition for treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), idiopathic and drug induced Parkinson's Disease and brain edema, and muscular spasms, migraine headaches, urinary incontinence, psychosis, convulsions, chronic or acute pain, ocular damage, retinopathy, retinal neuropathy, tinnitus, anxiety, emesis and tardive dyskinesia, in a mammal, comprising an AMPA receptor antagonizing effective amount of a compound of formula Ia and a pharmaceutically acceptable carrier.

This invention also relates to a method for treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), idiopathic and drug induced Parkinson's Disease and brain edema, and muscular spasms, migraine headaches, urinary incontinence, psychosis, convulsions, chronic or acute pain, ocular damage, retinopathy, retinal neuropathy, tinnitus, anxiety, emesis and tardive dyskinesia, in a mammal, comprising administering to a mammal requiring such treatment or prevention an AMPA receptor antagonizing effective amount of a compound of formula Ia.

The compounds of this invention include all stereoisomers and all optical isomers of compounds of the formula Ia (e.g., R and S enantiomers), as well as racemic, diastereomeric and other mixtures of such isomers.

The compounds of this invention may contain olefin-like double bonds. When such bonds are present, the compounds of the invention exist as cis and trans configurations and as mixtures thereof.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

Unless otherwise indicated, halo or halogen refer to fluorine, bromine, chlorine or iodine.

The bold lines in formulae Ia and Ib, depicted below, indicate that the bolded atoms, and the groups attached thereto, are sterically restricted so as to exist either orthogonally above the plane of the quinazolinone ring or orthogonally below the plane of the quinazolinone ring. This steric restriction is due to a rotational energy barrier preventing free rotation about the single bond connecting the quinazolinone ring to the "A, B and D" containing ring. This rotational energy barrier is a result of an inability of a $R^5$ substituent, ortho to the asterisked carbon, to rotate around the quinazoline nucleus.

In the compounds of formula Ia, the atoms "A and B" and the substituents thereon are sterically restricted so as to exist orthogonally above the plane of the quinazolinone ring when the ring is laid out with the vinyl group to the right of the quinazolinone ring. Compounds of formula Ia are denoted with (S) stereochemistry. In the compounds of formula Ib, the mirror image of the compounds of formula Ia and drawn below, the atoms "A, B and D" are sterically restricted so as to exist orthogonally above the plane of the quinazolinone ring when the vinyl group is laid out to the left of the quinazolinone ring. Compounds of the formula Ib are denoted with (R) stereochemistry. The compounds of formula Ia possess substantially all of the AMPA receptor antagonist activity whereas the compounds of formula Ib are essentially devoid of AMPA receptor antagonist activity.

DETAILED DESCRIPTION OF THE INVENTION

The compounds of formula I can be prepared according to the methods of Scheme 1. In the reaction Scheme and discussion that follow, A, B. D, K, L, M, P, Q, T, $R^2$, $R^3$, $R^5$, $R^9$, $R^{10}$, $R^{11}$, $R^{12}$, $R^{13}$, $R^{14}$, $R^{15}$, $R^{16}$, $R^{17}$, $Ph^2$, n, m, p, and s unless otherwise indicated, are as defined above for formula Ia.

SCHEME 1
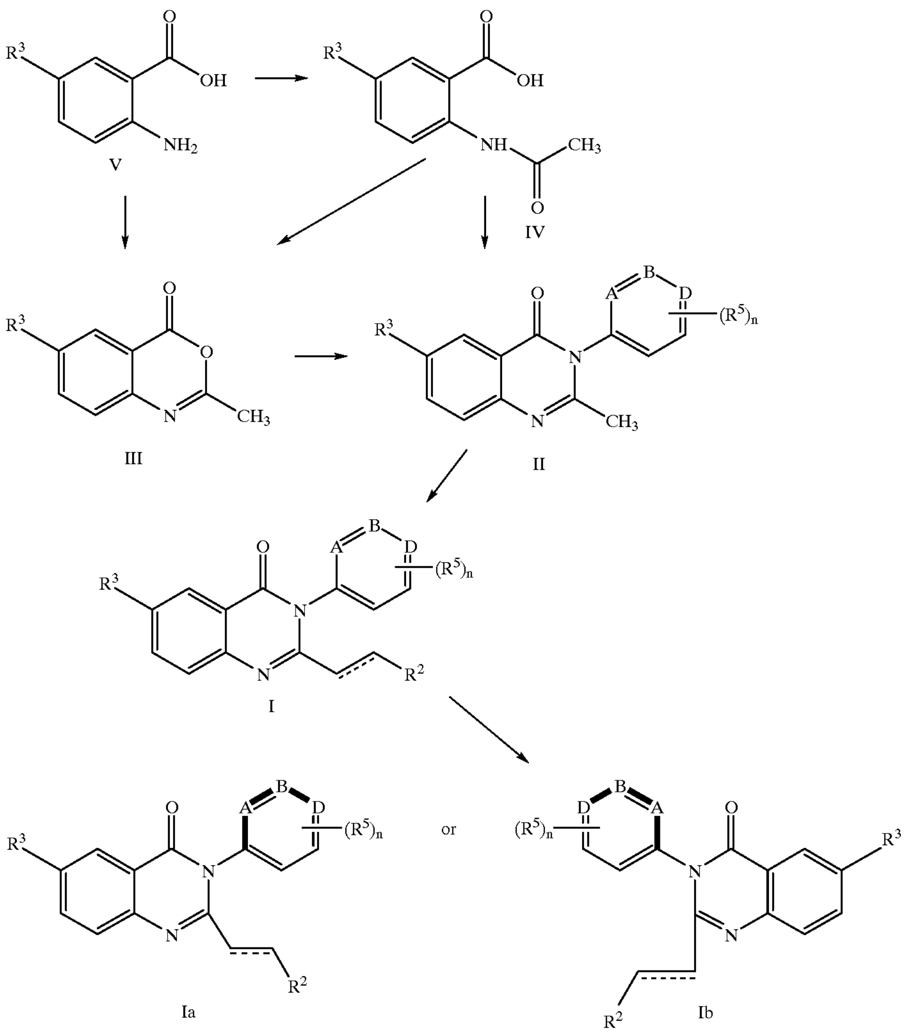
V
IV
III
II
I
Ia
or
Ib
SCHEME 2
V
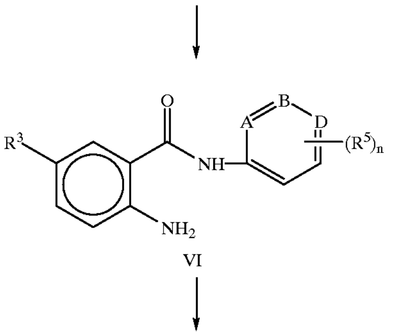
VI
-continued
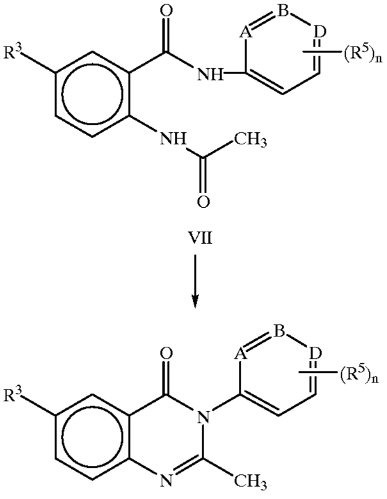
VII
II

SCHEME 3

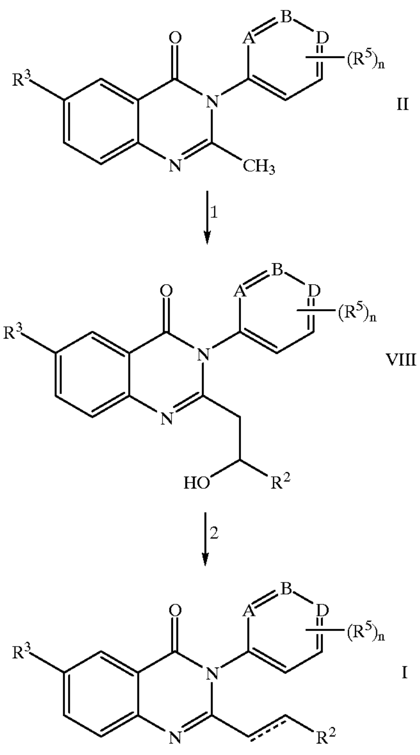

II

VIII

I

Scheme 1 refers to the preparation of compounds of the formula Ia or Ib from compounds of the formula V. Compounds of the formula V are commercially available or can be prepared by methods well known to those of ordinary skill in the art.

A compound of the formula V can be converted into an acetamide of the formula IV by reaction with acetyl chloride or acetic anhydride in the presence of a base in a reaction inert solvent. Suitable solvents include methylene chloride, dichloroethane, tetrahydrofuran and dioxane, preferably methylene chloride. Suitable bases include trialkylamines such as triethylamine and tributylamine, dimethylaminopyridine and potassium carbonate, preferably triethylamine. The temperature of the aforesaid reaction is in the range from about 0° C. to about 35° C. for about 1 hour to about 10 hours, preferably at about 25° C. for about 3 hours.

The acetamide of the formula IV is cyclized to a compound of the formula III by reaction with a dehydrating agent, in the presence of a catalyst, in dry reaction inert solvent. Suitable dehydrating agents include acetic anhydride, phosphrous pentoxide, dicyclohexylcarbodimide, and acetyl chloride, preferably acetic anhydride. Suitable catalysts include sodium or potassium acetate, acetic acid, p-toluene sulfonic acid, or boron trifluoride etherate, preferably sodium acetate. Suitable solvents include dioxane, toluene, diglyme or dichloroethane, preferably dioxane. The temperature of the aforesaid reaction is in the range from about 80° C. to about 110° C. for about 1 hour to about 24 hours, preferably at about 100° C. for about 3 to 10 hours.

Alternatively, the compound of formula V can be directly converted into a compound of formula III by reaction with acetic anhydride in the presence of an acid catalyst in a solvent. Suitable acid catalysts include acetic acid, sulfuric acid, or p-toluene sulfonic acid, preferably acetic acid. Suitable solvents include acetic acid, toluene or xylene, preferably acetic acid. The temperature of the aforesaid reaction is from about 20° C. to about 150° C. for about 10 minutes to about 10 hours, preferably at about 120° C. for about 2 to 5 hours.

The compound of formula II, formed by either of the above methods, is reacted with an amine of the formula

VIII

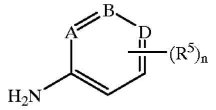

in a polar protic solvent in the presence of an acid catalyst to form a compound of the formula II. Suitable acid catalysts include acetic acid, p-toluene sulfonic acid or sulfuric acid, preferably acetic acid. Suitable polar protic solvents include acetic acid, methanol, ethanol or isopropanol, preferably acetic acid. The temperature of the aforesaid reaction is from about 20° C. to about 117° C. for about 1 hour to about 24 hours, preferably at about 117° C. for about 6 hours.

Alternatively, a compound of the formula IV can be directly converted to a compound of the formula II by reaction with a dehydrating agent, an amine of the formula VIII, and a base, in a reaction inert solvent. Suitable dehydrating agents include phosphorous trichloride, phosphorous oxychloride, phosphorous pentachloride or thionyl chloride, preferably phosphorous trichloride. Suitable bases include pyridine, lutidine, dimethylaminopyridine, triethylamine or N-methyl morpholine, preferably pyridine. Suitable solvents include toluene, cyclohexane, benzene or xylene, preferably toluene. Under some circumstances, when the combined reactants are a liquid, the reaction may be run neat. The temperature of the aforesaid reaction is from about 50° C. to about 150° C. for about 1 hour to about 24 hours, preferably at about 110° C. for about 4 hours.

The compound of formula II is reacted with an aldehyde of the formula $R^2CHO$ in the presence of a catalyst and a dehydrating agent in a suitable solvent to form a compound of the formula I, wherein the dashed line is double bond. Suitable catalysts include zinc chloride, sodium acetate, aluminum chloride, tin chloride, or boron trifluoride etherate, preferably zinc chloride or sodium acetate. Suitable dehydrating agents include acetic anhydride, methane sulfonic anhydride, trifluoroacetic anhydride or propionic anhydride, preferably acetic anhydride. Suitable polar solvents include acetic acid, dioxane, dimethoxyethane or propionic acid. The temperature of the aforesaid reaction is from about 60° C. to about 100° C. for about 30 minutes to about 24 hours, preferably at about 100° C. for about 3 hours.

Compounds of the formula I wherein the dashed line represents a single carbon-carbon bond may be prepared by hydrogenating the corresponding compounds wherein the dashed line represents a double carbon-carbon bond, using standard techniques that are well known to those skilled in the art. For example, reduction of the double bond may be effected with hydrogen gas ($H_2$), using catalysts such as palladium on carbon (Pd/C), palladium on barium sulfate ($Pd/BaSO_4$), platinum on carbon (Pt/C), or tris (triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C., as described in *Catalytic Hydrogenation in Organic Synthesis*, Paul Rylander, Academic Press Inc., San Diego, 1979, pp. 31–63. The following conditions are preferred: Pd on carbon, ethyl acetate at 25° C. and 15–20 psi of hydrogen gas pressure. This method also provides for introduction of hydrogen isotopes (i.e. deuterium, tritium) by replacing $^1H_2$ with $^2H_2$ or $^3H_2$ in the above procedure.

Compounds of the formula I can be separated into compounds of the formulae Ia and Ib by High Pressure Liquid Chromatography (HPLC) using a chiral HPLC column and eluting with an appropriate solvent. One of ordinary skill in the art will understand that many types of instruments, columns and eluents can be used to separate the individual atropisomers. Suitable HPLC instruments include LC SpiderLing®, Waters 4000®, Hewlett Packard 1050® and Analytical Grade Thermo Separation Products HPLC. Suitable HPLC's are configured according to methods well known to those of ordinary skill in the art. Such configuration invariably includes a pump, injection port and a detector. Suitable chiral columns can be purchased prepackaged or can be packed by one of ordinary skill in the art. Suitable chiral columns include chiral OA, OD, OG, AD and AS columns which can be purchased from Chiral Technologies Inc., 730 Springdale Drive, PO Box 564, Exton, Pa. 19341. One of ordinary skill in the art will appreciate that many other chiral columns, purchased from other vendors, would be adequate to separate the isomers of the invention. The packing material can also be purchased in different bead sizes. Suitable bead sizes for preparative separations are about 20 microns in diameter. Suitable bead sizes for analytical separation are about 10 microns in diameter.

Compounds of formula Ia, wherein a basic group is present, can also be resolved by treatment with an enantiomerically pure acid in a suitable solvent to form separable diasteriomeric salts. Suitable enantiomerically pure acids include camphor sulphonic acid, tartaric acid (and derivatives thereof), mandelic acid and lactic acid. Suitable solvents include alcohols, such as ethanol, methanol and butanol, toluene, cyclohexane, ether and acetone.

Alternatively, a compound of the formula V can be converted to a compound of the formula II according to the methods described in Scheme 2. The compound of formula II, so formed, can be converted into a compound of formula I according to the methods of Scheme 1. Referring to Scheme 2, a compound of the formula V is reacted with a coupling reagent, an amine of the formula VIII, and a base in a reaction inert solvent to form a compound of the formula VI. Examples of suitable coupling reagents which activate the carboxylic functionality are dicyclohexylcarbodiimide, N-3-dimethylaminopropyl-N'-ethylcarbodiimide, 2-ethoxy-1-ethoxycarbonyl-1,2-dihydroquinoline (EEDQ), carbonyl diimidazole (CDI), and diethylphosphorylcyanide. Suitable bases include dimethylaminopyridine (DMAP), hydroxybenzotriazole (HBT), or triethylamine, preferably dimethylaminopyridine. The coupling is conducted in an inert solvent, preferably an aprotic solvent. Suitable solvents include acetonitrile, dichloromethane, dichloroethane, and dimethylformamide. The preferred solvent is dichloromethane. The temperature of the aforesaid reaction is generally from about −30 to about 80° C., preferably about 0 to about 25° C.

The compound of formula VI is converted into a compound of the formula VII by reaction with acetyl chloride or acetic anhydride in the presence of a base in a reaction inert solvent. Suitable solvents include methylene chloride, tetrahydrofuran and chloroform, preferably methylene chloride. Suitable bases include trialkylamines such as triethylamine and tributylamine, dimethylaminopyridine and potassium carbonate, preferably triethylamine. The temperature of the aforesaid reaction is in the range from about 0° C. to about 35° C. for about 1 hour to about 10 hours, preferably at about 30° C. for about 3 hours.

The compound of formula VII is cyclized to a compound of formula II by reaction with triphenylphosphine, a base, and a dialkyl azodicarboxylate in a reaction inert solvent. Suitable bases include pyridine, triethylamine and 4-dimethylaminopyridine, preferably 4-dimethylaminopyridine. Suitable solvents include dimethylformamide, tetrahydrofuran and dioxane, preferably dioxane. The temperature of the aforesaid reaction is in the range from about 25° C. to about 125° C. for about 1 hour to about 24 hours, preferably at about 100° C. for about 8 to 15 hours. The compound of formula II can be converted into a compound of formula I according to the method described in Scheme 1.

Compounds of formula II can also be made according to the methods described in Miyashita, et al., *Heterocyclesl* 42, 2, 691–699 (1996).

In Scheme 3, the compound of formula 11 is converted to the corresponding compound of formula VIII by reacting II with a base, as lithium diisopropylamide, in a polar aprotic solvent such as tetrahydrofuran. The solution is stirred at a temperature between about −100° C. to about 0° C., preferably about −78° C., for a time period between about 15 minutes to about 1 hour, preferably about 30 minutes. The anionic product so formed is reacted with with a tetrahydrofuran solution of an aldehyde of the formula $R^2CHO$. The solution of aldehyde can be added to the anion solution (normal addition) or the anion solution can be added to the solution of the aldehyde (inverse addition). While both methods can be used to produce compounds of formula VII, inverse additional is preferred. The resulting reaction mixture is stirred for a time period between about 15 minutes to about 1 hour, preferably about 30 minutes, at a temperature between about −100° C., preferably about −78° C., and then is allowed to warm to ambient temperature. In reaction 2 of Scheme 3, the compound of formula VIII is converted to the corresponding compound of formula I by reacting VII with a dehydrating agent, such as trifluoroacetic anhydride, in dry reaction inert solvent, such as dioxane, toluene, diglyme or dichloroethane, preferably dioxane. The reaction mixture is stirred at a temperature between about 0° C. to about 50° C., preferably room temperature, for a time period between about 1 hour to about 14 hours, preferably about 12 hours.

Compounds of the formula I wherein the dashed line represents a single carbon-carbon bond may be prepared by hydrogenating the corresponding compounds wherein the dashed line represents a double carbon-carbon bond, using standard techniques that are well known to those skilled in the art. For example, reduction of the double bond may be effected with hydrogen gas ($H_2$), using catalysts such as palladium on carbon (Pd/C), palladium on barium sulfate ($Pd/BaSO_4$), platinum on carbon (Pt/C), or tris (triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C., as described in *Catalytic Hydrogenation in Organic Synthesis*, Paul Rylander, Academic Press Inc., San Diego, 1979, pp. 31–63. The following conditions are preferred: Pd on carbon, ethyl acetate at 25° C. and 15–20 psi of hydrogen gas pressure. This method also provides for introduction of hydrogen isotopes (i.e, deuterium, tritium) by replacing $^1H_2$ with $^2H_2$ or $^3H_2$ in the above procedure.

When $R^2$ is heteroaryl, one of ordinary skill in the art will understand that heteroaryl is selected from the group consisting of pyridin-2-yl, 1,3-pyrazin-4-yl, 1,4-pyrazin-3-yl, 1,3-pyrazin-2-yl, pyrrol-2-yl, 1,3-imidazol-4-yl, 1,3-imidazol-2-yl, 1,3,4-triazol-2-yl, 1,3-oxazol-4-yl, 1,3-oxazol-2-yl, 1,3-thiazol-4-yl, 1,3-thiazol-2-yl, 1,2,4-oxadiazol-3-yl, 1,2,4-oxadiazol-5-yl, fur-2-yl, 1,3-oxazol-5-yl, and 1,3,4-oxadiazol-2-yl, wherein said heteroaryl may optionally be substituted on any of the atoms capable of forming an additional bond, up to a maximum of three substituents.

Unless indicated otherwise, the pressure of each of the above reactions is not critical. Generally, the reactions will be conducted at a pressure of about one to about three atmospheres, preferably at ambient pressure (about one atmosphere)

The compounds of the formula Ia which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula Ia which are acidic in nature are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula Ia. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula Ia and the pharmaceutically acceptable salts thereof (hereinafter, also referred to as "the active compounds of the invention") are useful for the treatment of neurodegenerative and CNS-trauma related conditions and are potent AMPA receptor agonists and antagonists. The active compounds of the invention may therefore be used in the treatment or prevention of cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), idiopathic and drug induced Parkinson's Disease and brain edema, and muscular spasms, migraine headaches, urinary incontinence, psychosis, convulsions, chronic or acute pain, ocular damage, retinopathy, retinal neuropathy, tinnitus, anxiety, emesis and tardive dyskinesia.

The in vitro and in vivo activity of the compounds of the invention for AMPA receptor antagonism can be determined by methods available to one of ordinary skill in the art. One method for determining the activity of the compounds of the invention is by inhibition of pentylenetetrazol (PTZ)-induced seizures. Another method for determining the activity of the compounds of the invention is by blockage of AMPA receptor activation-induced $^{45}Ca^{2+}$ uptake.

One specific method for determining inhibition of pentylenetetrazol (PTZ)-induced seizures is as follows. The activity of the compounds of the invention for inhibition of pentylenetetrazol (PTZ)-induced seizures in mice can be determined according to the following procedure. This assay examines the ability of compounds to block seizures and death produced by PTZ. Measures taken are latency to clonic and tonic seizures, and death. $ID_{50}$s are determined based on percent protection.

Male CD-1 mice from Charles River, weighing 14–16 g on arrival and 25–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

Mice are administered the test compounds or vehicle (i.p., s.c., or p.o.) and are placed into plexiglass cages in groups of five. At a predetermined time after these injections, mice are given an injection of PTZ (i.p., 120 mg/kg) and placed into individual plexiglass cages. Measures taken during this five minute test period are: (1) latency to clonic seizures, (2) latency to tonic seizures, and (3) latency to death. Treatment groups are compared to the vehicle-treated group by Kruskal-Wallis Anova and Mann-Whitney U tests (Statview). Percent protection is calculated for each group (number of subjects not showing seizure or death as indicated by a score of 300 secs) at each measure. $ID_{50}$'s are determined by probit analysis (Biostat).

Another method for determining the activity of the compounds is to determine the effect of the compounds on motor coordination in mice. This activity can be determined according to the following procedure.

Male CD-1 mice from Charles River, weighing 14–16 g on arrival and 23–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

The apparatus used in these studies consists of a group of five 13.34×13.34 cm wire mesh squares suspended on 11.43 cm steel poles connected to a 165.1 cm pole which is elevated 38.1 cm above the lab bench. These wire mesh squares can be turned upside-down.

Mice are administered test compounds or vehicle (i.p., s.c., or p.o) and are placed into plexiglass cages in groups of five. At a predetermined time after these injections, mice are placed on top of the wire mesh squares and flipped so that they are suspended upside-down. During the one minute test, mice are rated 0 if they fall off the screen, m 1 if they hang on upside-down, or 2 if they climb up onto the top. Treatment groups are compared to the vehicle-treated group with Kruskal-Wallis and Mann-Whitney U tests (Statview).

One specific method for determining AMPA receptor activation-induced $^{45}Ca^{2+}$ uptake is described below.

Neuronal Primary Cultures

Primary cultures of rat cerebellar granule neurons are prepared as described by Parks, T. N., Artman, L. D., Alasti, N., and Nemeth, E. F., Modulation Of N-Methvl-D-Aspartate Receptor-Mediated Increases In Cytosolic Calcium In Cultured Rat Cerebellar Granule Cells, Brain Res. 552, 13–22 (1991). According to this method, cerebella are removed from 8 day old CD rats, minced into 1 mm pieces and incubated for 15 minutes at 37° C. in calcium-magnesium free Tyrode's solution containing 0.1% trypsin. The tissue is then triturated using a fine bore Pasteur pipette. The cell suspension is plated onto poly-D-lysine coated 96-well tissue culture plates at $10^5$ cells per well. Medium consists of Minimal Essential Medium (MEM), with Earle's salts, 10% heat inactivated Fetal Bovine Serum, 2 mM L-glutamine, 21 mM glucose, Penicillin-Streptomycin (100 units per ml) and 25 mM KCl. After 24 hours, the medium is replaced with fresh medium containing 10 μM cytosine arabinoside to inhibit cell division. Cultures should be used at 6–8 DIV.

AMPA Receptor Activation-induced $^{45}Ca^{2+}$ Uptake

The effects of drugs on AMPA receptor activation-induced $^{45}Ca^{2+}$ uptake can be examined in rat cerebellar granule cell cultures. Cultures in 96 well plates are preincubated for approximately 3 hours in serum free medium and then for 10 minutes in a $Mg^{2+}$-free balanced salt solution (in mM: 120 NaCl, 5 KCl, 0.33 $NaH_2PO_4$1.8 $CaCl_2$, 22.0 glucose and 10.0 HEPES at pH 7.4) containing 0.5 mM DTT, 10 uM glycine and drugs at 2× final concentration. The reaction is started by rapid addition of an equal volume of the balanced salt solution containing 100 μM of the AMPA receptor agonist kainic acid and $^{45}Ca^{2+}$ (final specific activity 250 Ci/mmol). After 10 minutes at 25° C., the reaction is stopped by aspirating the $^{45}Ca^{2+}$-containing solution and washing the cells 5× in an ice cold balanced salt solution containing no added calcium and 0.5 mM EDTA. Cells are then lysed by overnight incubation in 0.1% Triton-X100 and radioactivity in the lysate is then determined. All of the compounds of the invention, that were tested, had $IC_{50}$s of less than 500 nM.

The compositions of the present invention may be formulated in a conventional manner using one or more pharmaceutically acceptable carriers. Thus, the active compounds of the invention may be formulated for oral, buccal, transdermal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

For transdermal administration the composition may take the form of patches, creams, ointments or iontophoresis formulated in conventional manner such as described in U.S. Pat. Nos. 5,004,610 or 5,364,630 issued Apr. 2, 1991 and Nov. 15, 1994 respectively.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g, dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., stroke) is 0.01 to 20 mg/kg of the active ingredient per unit dose which could be administered, for example, 1 to 4 times per day.

Aerosol formulations for treatment of the conditions referred to above (e.g., stroke) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Melting points are uncorrected. All NMR data were recorded at 250, 300 or 400 MHz in deuterochloroform unless otherwise specified and are reported in parts per million (δ) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectrum were performed using chemical impact conditions. Ambient or room temperature refers to 20–25° C.

EXAMPLE 1

(S)-6-Fluoro-3-(2-methyl-pyridin-3-yl)-2-[2-(2-methyl-thiazol-4-yl)-vinyl]-3H-quinazolin-4-one Mesylate and (R)-6-fluoro-3-(2-methyl-pyridin-3-yl)-2-[2-(2-methyl-thiazol-4-yl)-vinyl]-3H-quinazolin-4-one Mesylate Racemic-fluoro-3-(2-methyl-pyridin-3-yl)-2-[2-(2-methyl-thiazol-4-yl)-vinyl]-3H-quinazolin-4-one (0.090 g) was dissolved in 0.1% diethylamine/isopropanol (60 mL) (final concentration 1.5 mg/mL) and applied to a preparative HPLC column (5×50 cm Chiralcel AD) and eluted with 85/15/0.1 heptane/isopropanol/diethylamine at a flow rate of 100 ml/min. The eluent was monitored with ultraviolet detection at 265 nM. Two fractions were collected, the first component centered around an elution time of 60 min and the second around an elution time of 75 min. The total cycle time for the run was 90 min. The eluent from 4 cycles with elution time of 60 min were combined and concentrated to give an oily tan solid. The solid was triturated with ether/hexane to afford 0.175 g of tan powder. This powder was nearly dissolved in magnetically stirred ethyl acetate (15 mL) and treated with 1 N methanesulfonic acid in ethyl acetate (0.462 mL, 0.462 mmol). A salt immediately began precipitating. The mixture was stirred for 6 hours, at which time the product was collected, rinsed with ethyl acetate, and dried to afford 0.144 g of (+)-6-fluoro-3-(2-methyl-pyridin-3-yl)-2-[2-(2-methyl-thiazol-4-yl)-vinyl]-3H-quinazolin-4-one mesylate as a light yellow solid.

Melting point 145–146° C. (The melted material equilibrated and resolidified. Continued heating resulted in a second melting range of 210–225° C.) The product also had: NMR (methanol$_{d4}$) δ 9.02 (dd, J=1.5, 6 Hz, 1H), 8.69 (dd, J=1.5, 8.3 Hz, 1H), 8.17 (dd, J=6, 8.2 Hz, 1H), 8.01 (d, J=15 Hz, 1H), 7.92–7.85 (m, 2H), 7.76 (s,1H), 7.72 (dt, J=3, 8.7 Hz, 1H), 6.58 (d, J=15 Hz, 1H), 2.68 (s, 3H), 2.67 (s, 3H), 2.63 (s, 3H); $[\alpha]^D$=+18.9° (c=0.18 in methanol).

The eluent from the same four cycles with elution time of 75 min were concentrated and converted to mesylate salt in the same fashion to afford 0.144 g of (−)-6-fluoro-3-(2-methyl-pyridin-3-yl)-2-[2-(2-methyl-thiazol-4-yl)-vinyl]-3H-quinazolin-4-one mesylate as a light yellow solid which had: $[\alpha]^D$=−18.3° (c=0.175 in methanol). All other physical characteristics were identical to the atropisomer.

EXAMPLES 2–7

Examples 2–7 were prepared according to methods analogous to those of Example 1.

TABLE 1

| Example | Name | Column; Mobile Phase; Flow rate | UV (nm) | Retention Time (minutes) |
|---|---|---|---|---|
| 2 | 6-Fluoro-3-(2-methyl-pyridin-3-yl)-2-[2-(4-methyl-thiazol-2-yl)-vinyl]-3H-quinazolin-4-one | Chiralpak AD; 70/30 hexane/isopropanol + 0.1 diethyl amine; 1 mL/min | 360 | 6.825 |
| 3 | 6-Fluoro-3-(2-methyl-pyridin-3-yl)-2-[2-(4-methyl-thiazol-2-yl)-vinyl]-3H-quinazolin-4-one | Chiralpak AD; 70/30 hexane/isopropanol + 0.1 diethyl amine 1 mL/min | 360 | 9.674 |
| 4 | 2-{2-[6-Fluoro-3-(2-methylpyridin- 3-yl)-4-oxo-3,4-dihydroquinazolin- 2-yl]-vinyl}-benzonitrile | Chiralpak AD; 70/30 hexane/isopropanol + 0.1 diethyl amine; 1 mL/min | 335 | 9.861 |
| 5 | 2-{2-[6-Fluoro-3-(2-methylpyridin- 3-yl)-4-oxo-3,4-dihydroquinazolin- 2-yl]-vinyl}-benzonitrile | Chiralpak AD; 70/30 hexane/isopropanol + 0.1 diethyl amine; 1 mL/min | 335 | 13.951 |
| 6 | 2-{2-[3-(2-Chloro-pyridin-3-yl)-6-fluoro-4-oxo-3,4-dihydroquinazol-in-2-yl]-vinyl}-benzonitrile | Chiralpak AD; 70/30 hexane/isopropanol + 0.1 diethyl amine; 1 mL/min | 335 | 11.372 |
| 7 | 2-{2-[3-(2-Chloro-pyridin-3-yl)-6-fluoro-4-oxo-3,4-dihydroquinazol-in-2-yl]-vinyl}-benzonitrile | Chiralpak AD; 70/30 hexane/isopropanol + 0.1 diethyl amine; 1 mL/min | 335 | 20.264 |

EXAMPLES 8–9

All HPLC analytical separation experimental conditions described below were carried out with a Hewlett Packard model 1050 HPLC. The dimensions of the analytical columns were 4.6 mm×25 cm and the stationary phase particle size was 10 micron. All samples were dissolved in methanol.

(S)-3-(2-Chloro-pyridin-3-yl)-6-fluoro-2-[2-(fluorophenyl)-vinyl]-3H-quinazolin-4-one

| | |
|---|---|
| Column | Chiralcel OD |
| Mobile Phase | 80/20 hexane/isopropyl alcohol with 0.1% diethylamine |
| Flow Rate | 1 mL/min |
| Detection | UV (250 nM) |
| Retention Time (first atropisomer) | 18.697 min |
| Retention Time (second atropisomer) | 22.102 min |

(S)-6-Fluoro-3-(2-methyl-pyridin-3-yl)-2-[2-(2-methyl-thiazol-4-yl)-vinyl]-3H-quinazolin-4-one

| | |
|---|---|
| Column | Chiralcel OD |
| Mobile Phase | 90/10 hexane/isopropyl alcohol with 0.1% diethylamine |
| Flow Rate | 1 mL/min |
| Detection | UV (250 nM) |
| Retention Time (first atropisomer) | 38.038 min |
| Retention Time (second atropisomer) | 45.032 min |

PREPARATION 1

3-(2-Chlorophenyl)-2-[2-(6-diethylaminomethylpyridin-2-yl)-vinyl]-6-fluoro-3H-quinozolin-4-one

Method A

6-Fluoro-2-methylquinoxalin-4-one

A solution of 12.95 g (70.0 mmol) of 2-nitro-5-fluorobenzoic acid in 200 mL of glacial acetic acid and 20 mL of acetic anhydride was treated with 0.625 g of 10% palladium on carbon are reduced at an initial pressure of 54.5 psi. Hydrogen uptake was complete after two hours. The catalyst was removed by filtration and the filtrate was heated at reflux for two hours at which time TLC (1:1 hexane/ethyl acetate) indicated that the reaction was complete. The reaction mixture was evaporated to a semicrystalline mass which was broken up in a minimum amount of 2-propanol and stirred in an ice bath for one hour. The crystalline solid was separated by filtration, washed with minimal cold 2-propanol and air dried to give 5.79 g (46%) of the desired product as a brown solid, m.p. 127.5–128.5° C.

A synthesis of 5-fluoro-2-nitrobenzoic acid is described by Slothouwer, J. H., *Recl. Trav. Chim. Pays-Bas* 33, 336 (1914).

Method B 3-(2-Chlorophenyl)-6-fluoro-2-methyl-4-(3H)-guinazolinone

A solution of 2.50 g (14.0 mmol) of 6-fluoro-2-methylquinoxalin-4-one and 1.96 g (15.4 mmol) of 2-chloroaniline in about 20 mL of glacial acetic acid was heated at reflux under a nitrogen atmosphere for 6 hours. Most of the solvent was evaporated from the cooled reaction mixture and the residues were taken up in ethanol and refrigerated. After 6 days in the refrigerator, the formed crystals were filtered off, washed with minimal cold ethanol and air dried to give 1.79 g (44%) of the product. m.p. 137–138° C.

Method C 6-(2-[3-(2-Chlorophenyl)-6-fluoro-4-oxo-3,4-dihydroquinazolin-2-yl-vinyl)pyridine-2-carbaldehyde A catalytic amount (about 100 mg) of anhydrous zinc chloride was added to a solution of 576 mg (2.0 mmol) of 3-(2-chlorophenyl)-6-fluoro-2-methyl-4(3H)-quinazolinone and 270 mg (2.0 mmol) of 2,6-pyridinedicarboxaldehyde in 20–25 mL of dioxane and 1.0 mL of acetic anhydride. The reaction mixture was heated at reflux under a nitrogen atmosphere for 3 hours until TLC indicated that the starting materials had been consumed. The cooled reaction mixture was poured into water and the mixture was extracted with ethyl acetate. The combined extracts were dried with brine and magnesium sulfate, treated with decolonizing carbon and filtered and the solvent was removed to give the desired product. This was taken up in 2:1 ether/pentane and the crystals were filtered to give 266 mg of the product, 33%, m.p. 247–248° C.

A synthesis of pyridine-2,6-dicarboxaldehyde is described by Papadopoulos, et. al., J. Org. Chem. 31, 615 (1966).

Method D 3-(2-Chlorophenyl)-2-[2-(6-diethylaminomethylpyridin-2-yl)-vinyl]-6-fluoro-3H-quinozolin-4-one A solution of 65 mg (0.16 mmol) of 6-{2-[3-(2-chlorophenyl)-6-fluoro-4-oxo-3,4-dihydroquinazolin-2-yl)-vinyl)pyridine-2-carbaldehyde in 10 mL of methylene chloride at room temperature under a nitrogen atmosphere was treated with 3 drops of diethylamine and 73 mg (0.34 mmol) of sodium triacetoxyborohydride. After stirring for 2 ½ hour at room temperature, the solvent was evaporated and the residues were partitioned between dilute hydrochloric acid and either and stirred for 30 minutes. The ethereal layer was separated and the aqueous was extracted once again with ether the ethereal extracts were discarded. The aqueous acidic solution was adjusted to a pH of about 14 with 10% sodium hydroxide (ice bath cooling) and was then extracted with ether twice. The combined ethereal extracted were dried with brine and with magnesium sulfate and the solvent was evaporated. After one attempt to form a mesylate salt, the reworked free base in ethyl acetate was treated with 7.5 mg (0.06 mmol) of maleic acid dissolved in a little ethyl acetate. Crystals formed from the resulting solutions which were filtered and washed with ethyl acetate to give 22 mg of the monomaleate salt, (24%), m.p. 170.5–171.5° C.

PREPARATION 2–19

Preparations 2–19 were made according to methods analogous to those of Preparation 1.

TABLE 1

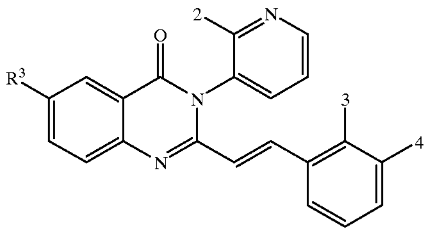

| Prep | $R^3$ | 2 | 3 | 4 | NMR |
|---|---|---|---|---|---|
| 2 | H | Cl | F | H | ($CDCl_3$) δ6.38(1H, d, J=13), 7.00–7.11(2H, m), 7.25–7.34(2H, m), 7.46–7.52(2H, m), 7.77–7.84(3H, m), 8.10(1H, d, J=13), 8.29(1H, d, J=6), 8.61(1H, m). |
| 3 | F | Cl | F | H | ($CDCl_3$) δ6.36(1H, d, J=13), 7.00–7.12(2H, m), 7.25–7.33(2H, m), 7.49–7.58(2H, m), 7.76–7.86(2H, m), 7.91–7.94(1H, d, J=6), 8.08(1H, d, J=13), 8.61(1H, m). |
| 4 | F | $CH_3$ | F | H | ($CDCl_3$) δ2.37(3H, s), 6.35(1H, d, J=13), 7.00–7.10(2H, m); 7.25–7.32 (2H, m), 7.37–7.41(1H, m), 7.51–7.58(2H, m), 7.81–7.85(1H, m), 7.91–7.94(1H, d, J=6), 8.06(1H, d, J=13), 8.71(1H, m). |
| 5 | F | Cl | H | 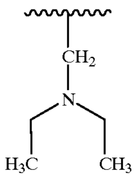 | ($CDCl_3$) δ1.00(6H, t, J=6), 1.98(4H, q, J=6), 3.50(2H, s), 6.29(1H, d, J=13), 7.16–7.66(6H, m), 7.72–7.85 (2H, m), 7.92(1H, d, J=6), 8.03(1H, d, J=13), 8.62(1H, m). |
| 6 | F | Cl | H | CHO | ($CDCl_3$) δ6.29(1H, d, J=13), 7.47–7.62(4H, m), 7.68–7.96(5H, m), 8.07 (1H, d, J=13), 8.63(1H, m), 9.98(1H, s). |
| 7 | H | Cl | H | CHO | ($CDCl_3$) δ6.31(1H, d, J=13), 7.48–7.61(5H, m), 7.78–7.84(4H, m), 8.10 (1H, d, J=13), 8.30(1H, d, J=6), 8.63 (1H, m), 10.00(1H, s). |
| 8 | F | Cl | H | 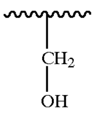 | ($CDCl_3$) δ4.66(2H, s), 6.20(1H, d, J=13), 7.22–7.32(5H, m), 7.50–7.58 (2H, m), 7.75–7.83(2H, m), 7.90–7.93(1H, m), 8.02(1H, m, J=13), 8.61 (1H, m). |
| 9 | F | Cl | CN | H | ($CDCl_3$) δ6.50(1H, d, J=13), 7.39–7.68(6H, m), 7.78–7.95(3H, m), 8.25 (1H, d, J=13), 8.62(1H, m). |
| 10 | F | Cl | H | 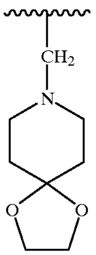 | ($CDCl_3$) δ1.72(4H, broad t), 2.50(4H, broad t), 3.49(2H, s), 3.96(4H, s), 6.21(1H, d, J=13), 7.22–7.35(4H, m), 7.51–7.58(2H, m), 7.77–7.84 (2H, m), 7.90–7.94(1H, m), 8.03 (1H, d, J=13), 8.64(1H, m). |

TABLE 1-continued

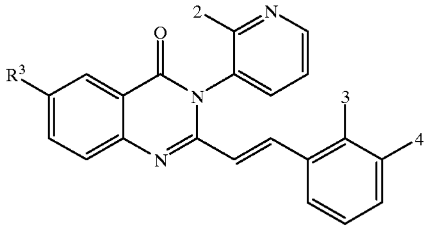

| Prep | $R^3$ | 2 | 3 | 4 | NMR |
|---|---|---|---|---|---|
| 11 | F | Cl | H | 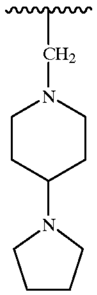 | ($CDCl_3$) δ1.47–1.61(1H, m), 1.73–2.10(12H, m), 2.50–2.60(3H, m), 2.77–2.88(1H, m), 3.43(2H, s), 6.70 (1H, d, J=13), 7.18–7.33(4H, m), 7.50–7.61(2H, m), 7.74–7.83(2H, m), 7.89–7.96(1H, m), 8.01(1H, d, J=13), 8.67(1H, m). |
| 12 | H | Cl | CN | H | ($CDCl_3$) δ6.52(1H, d, J=13), 7.38–7.86(9H, m), 8.27(1H, d, J=13), 8.30 (1H, s), 8.61(1H, m). |
| 13 | H | $CH_3$ | CN | H | ($CDCl_3$) δ2.39(3H, s), 6.47(1H, d, J=13), 7.35–7.42(3H, m), 7.49–7.60 (3H, m), 7.64–7.67(1H, m), 7.76–7.86(2H, m), 8.29(1H, m), 8.31(1H, d, J=13), 8.70(1H, m). |
| 14 | H | $CH_3$ | F | H | ($CDCl_3$) δ2.38(3H, s), 6.38(1H, d, J=10), 7.00–7.10(2H, m), 7.25–7.32 (2H, m), 7.36–7.40(1H, m), 7.47–7.58(2H, m), 8.812H, s), 8.11(1H, d, J=10), 8.31(1H, J=6), 8.70(1H, m). |
| 15 | F | Cl | OH | H | ($CDCl_3$/DMSO-$d_6$) δ6.34(1H, d, J=10), 6.55–6.68(2H, m), 6.91–7.02(2H, m), 7.32–7.39(2H, m), 7.61–7.79 (3H, m), 8.00(1H, d, J=10), 8.41(1H, m). |
| 16 | F | $CH_3$ | CN | H | ($CDCl_3$) δ2.39(3H, s), 6.45(1H, d, J=10), 7.37–7.43(3H, m), 7.49–7.60 (3H, m), 7.67(1H, d, J=6), 7.85–7.96 (2H, m), 8.28(1H, d, J=10), 8.72(1H, m). |
| 17 | Cl | $CH_3$ | F | H | ($CDCl_3$) δ2.38(3H, s), 6.37(1H, d, J=15), 7.01–7.12(2H, m), 7.24–7.34 (2H, m), 7.35(1H, m), 7.57(1H, d, J=6), 7.76(2H, m), 8.12(1H, d, J=15), 8.26(1H, s), 8.73(1H, m). |

PREPARATION 18

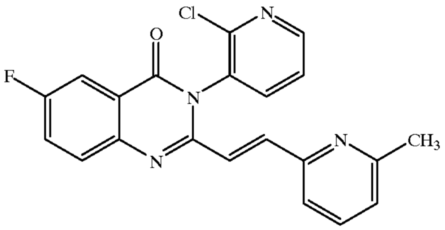

NMR: ($CDCl_3$) δ 2.44 (3H, s), 6.83 (1H, D, J=13), 7.04 (1H, d, J=10), 7.13 (1H, d, J=10), 7.50–7.58 (3H, m), 7.78–7.84 (2H, m), 7.92 (1H, m), 7.96 (1H, d, J=10), 8.61 (1H, m).

PREPARATION 19

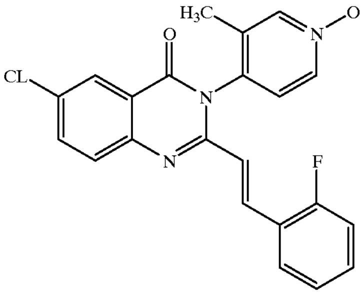

NMR: ($CDCl_3$) δ 2.09 (3H, s), 6.45 (1H, d, J=15), 7.03–7.18 (3H, m), 7.31–7.40 (2H, m), 7.75 (2H, s), 8.14 (1H, d, J=15), 8.22–8.71 (3H, m).

PREPARATION 20

6-Fluoro-3-(2-methyl-pyridin-3-yl)-2-[2-(2-methyl-thiazol-4-yl)-vinyl]-3H-quinazolin-4-one and its Mesylate Salt Anhydrous zinc chloride (2.7 g, 20 mmol) was fused with a nitrogen purge in a round bottom flask with an open flame. The reaction vessel was allowed to return to ambient temperature, then dioxane (150 mL) was added. To this mixture was added 6-fluoro-2-methyl-3-(2-methyl-pyridin-3-yl)-3H-quinazolin-4-one (2.6 g, 10 mmol), acetic anhydride (2.8 mL, 30 mmol), and 2-methylthiazole-4-carboxaldehyde (3.7 g, 30 mmol). The reaction was refluxed for 2 hours, then cooled to ambient temperature, and diluted with water. Sodium carbonate was added until the mixture was basic. Once the mixture was basic it was repeatedly extracted with chloroform. The combined chloroform layers were washed with water and brine and finally dried over sodium sulfate and concentrated to leave a dark residue. This residue was treated with methanol and concentrated (effectively azeotroping any residual chloroform from the residue). This process was repeated until a brown solid was formed. The solid was triturated with ether (twice), filtered and dried to afford 3.1 g (82%) of 6-fluoro-3-(2-methyl-pyridin-3-yl)-2-[2-(2-methyl-thiazo-4-yl)-vinyl]-3H-quinazolin-4-one as tan solid.

Melting Point: 223–224° C. NMR δ 8.70 (dd, J=1.5, 5 Hz, 1H), 7.90 (dd partially obscurred, J=3 Hz, 1H), 7.89 (d, J=15 Hz, 1H), 7.78 (dd, J=5, 9 Hz, 1 H), 7.54 (m, 2H), 7.39 (dd, J=5, 8 Hz, 1H), 7.23 (s, 1H), 6.57 (d, J=15 Hz, 1 H), 2.61 (s, 3H), 2.36 (s, 3H). Analysis calculated for $C_{20}H_{15}FN_4OS$ 0.5 $H_2O$: C, 62.06; H, 4.13; N, 14.58. Found: C, 62.39; H, 3.96; N, 14.33.

A sample was dissolved in ethyl acetate and treated with 1 N methanesulfonic acid in ethyl acetate to form the mesylate salt. The precipitate was collected, rinsed with ethyl acetate and dried to afford 6-fluoro-3-(2-methyl-pyridin-3-yl)-2-[2-(2-methyl-thiazol-4-yl)-vinyl]-3H-quinazolin-4-one mesylate as a light yellow solid.

Melting point: 230–231° C. NMR (methanol$_{d4}$) δ 9.01 (dd, J=1.2, 5.8 Hz, 1H), 8.65 (dd, J=1.3, 8.2 Hz, 1H), 8.15 (dd, J=5.9, 8.2 Hz, 1H), 8.00 (d, J=15 Hz, 1H), 7.88 (sym m, 2H), 7.71 (m, 2H), 6.56 (d, J=15 Hz, 1H), 2.68 (s, 3H), 2.65 (s, 3H), 2.62 (s, 3H). Analysis calculated for $C_{20}H_{15}FN_4OS$ $CH_3SO_3H$ 0.75 $H_2O$: C, 51.69; H, 4.20; N, 11.48. Found: C, 51.80; H, 4.18; N, 11.35.

PREPARATION 21

The compounds in table 1 were made by essentially the same procedures as exemplified by preparation 64.

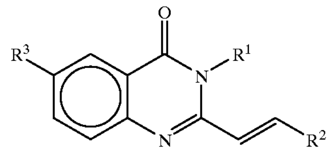

| Prep | $R^3$ | $R^2$ | $R^1$ | Physical Data |
|---|---|---|---|---|
| 21 | F | 2-dimethylamino-methylthiazol-4-yl | 2-chloropyrid-3-yl | NMR δ8.69(br d, J=4.3 Hz, 1H), 7.92(m, 2H), 7.78 (m, 2H), 7.54(m, 3H), 6.58 (d, J=14.7Hz, 1H), 4.34 (br s, 2H), 2.74(br s, 6H). |
| 22 | F | 2-dimethylamino-methylthiazol-4-yl | 2-methylpyrid-3-yl | NMR δ8.67(d, J=4.7Hz, 1H), 7.90(d, J=15Hz, 1H), 7.89(m, 1H), 7.76(dd, J=5, 9Hz, 1H), 7.51(m, 2H), 7.36(m, 1H), 7.34(s, 1H), 6.55(d, J=15Hz, 1H), 3.70(s, 2H), 2.34(s, 9H). |
| 23 | F | 2-methyloxazol-4-yl | 2-methylpyrid-3-yl | mp 223° C. NMR δ8.69(d, J=3.5Hz, 1H), 7.89(dd, J=3, 8.3Hz, 1H), 7.79(d, J=15Hz, 1H), 7.76(dd, J=5, 9Hz, 1H), 7.64(s, 1H), 7.53(m, 2H), 7.38(m, 1H), 6.41(d, J=15Hz, 1H), 2.37(s, 3H), 2.35(s, 3H). |
| 24 | F | thiazol-2-yl | 2-chloropyrid-3-yl | mp 195° C. NMR δ8.61(dd, J=1.7, 5Hz, 1H), 8.10(d, J=15Hz, 1H), 7.92(dd, J=3, 8.2Hz, 1H), 7.82–7.72(m, 3H), 7.57–7.49(m, 2H), 7.37(d, J=3.4Hz, 1H), 6.64(d, J=15Hz, 1H). |
| 25 | F | thiazol-2-yl | 2-methylpyrid-3-yl | mp 176° C. NMR δ8.70(dd, J=1.7, 4.7Hz, 1H), 8.09(d, J=15Hz, 1H), 7.91(dd, J=3, 8.3Hz, 1H), 7.89–7.78(m, 2H), 7.55(m, 2H), 7.38–7.34(m, 2H), 6.62(d, J=15Hz, 1H), 2.35(s, 3H). |

-continued

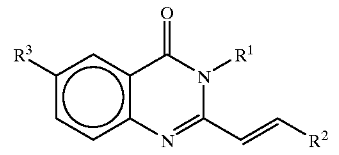

| Prep | $R^3$ | $R^2$ | $R^1$ | Physical Data |
|---|---|---|---|---|
| 26 | F | 4-methylthiazol-2-yl | 2-methylpyrid-3-yl | mp 178–180° C. NMR δ8.70(d, J=4Hz, 1H), 8.04(d, J=15Hz, 1H), 7.91(br d, J=8Hz, 1H), 7.79(dd, J=5, 8.7Hz, 1H), 7.55–7.53(m, 2H), 7.40–7.37 (m, 1H), 6.91(s, 1H), 6.55 (d, J=15Hz, 1H), 2.40(s, 3H), 2.36(s, 3H). |

PREPARATION 27

2-Dimethylaminomethylthiazole-4-carboxaldehyde

To a slurry of 2-dimethylaminothioacetamide hydrochloride (7.7 g, 50 mmol) in ethanol (100 mL) was added ethyl bromopyruvate (6.3 mL). The mixture was refluxed 6 h and then cooled to room temperature. More ethyl bromopyruvate (3.2 mL for a total of 75 mmol) was added and the reaction was refluxed 2.5 h more. The mixture was cooled to ambient temperature and concentrated at reduced pressure. The residue was partitioned between water and ethyl acetate and brought to pH 10 with addition of solid potassium carbonate. The phases were separated and the aqueous layer was extracted with ethyl acetate. The combined organic phase was washed with water and brine, then it was dried over sodium sulfate and concentrated to afford an amber oil. This oil was purified by flash chromatography on silica gel (120 g). Elution proceeded as follows: 2% methanol/chloroform, 200 mL, forerun; 10% methanol/chloroform, 75 mL, nil; 750 mL, 10.7 g (100%) of ethyl 2-dimethylaminomethylthiazole-4-carboxylate as a clear yellow oil which had: NMR δ 8.07 (d, J=1.4 Hz, 1H), 4.32 (q, J=7 Hz, 2H), 3.73 (s, 2H), 2.28 (s, 6H), 1.31 (t, J=7 Hz, 3H). The material was suitable for use without further purification.

To a mixture of lithium aluminum hydride (4.5 g, 119 mmol) in ice cold tetrahydrofuran (100 mL) was added ethyl 2-dimethylaminomethylthiazole-4-carboxylate (8.5 g, 39.7 mmol in 40 mL of tetrahydrofuran) dropwise over 40 min maintaining an internal temperature of 5–10° C. The mixture was stirred at this temperature range for 90 min. The reaction was carefully quenched with saturated aqueous ammonium chloride (30 mL). The resulting gray slurry was stirred 15 min and filtered through celite. The pad was well washed with ethyl acetate. The filtrate was washed with brine and dried over sodium sulfate. Concentration of this organic solution gave 4.2 g (62%) of 2-dimethylaminomethyl-4-hydroxymethylthiazole as an amber oil which had NMR δ 7.12 (s, 1H), 4.71 (s, 2H), 3.73 (s, 2H), 2.50 (br s, 1H), 2.32 (s, 6H). The material was used without further purification.

A solution of 2-dimethylaminomethyl-4-hydroxymethylthiazole (4.2 g, 27.3 mmol) in methylene chloride (200 mL) was treated with Dess-Martin reagent (14.5 g, 34.1 mmol). The mixture was stirred at ambient temperature 24 h. Additional Dess-Martin reagent (2.9 g) was added and the mixture was stirred 4 h more. The reaction was quenched by addition of saturated aqueous sodium thiosulfate (100 mL) and the pH of the resulting mixture was adjusted to 10 by addition of solid potassium carbonate. The two phase mixture was filtered. The phases were separated from the filtrate and the aqueous layer was extracted with methylene chloride. The combined organic layer was washed with brine, dried over sodium sulfate, and concentrated to afford a yellow solid. This solid was purified by flash chromatography on silica gel (50×130 mm) eluting first with chloroform (200 mL) and then 2% methanol/chloroform collecting 25 mL fractions. Fractions 51–80 were combined and concentrated to leave 2.9 g of a milky yellow oil. This oil was triturated with 50% ethereal chloroform and a solid was removed by filtration. The filtrate was concentrated to yield 2.6 g (62%) of 2-dimethylaminomethylthiazole-4-carboxaldehyde as a yellow oil which had: NMR δ 9.95 (s, 1H), 8.14 (s, 1H), 3.81 (s, 2H), 2.36 (s, 6H). This product was used without further purification.

PREPARATION 28

2-Methyloxazole-4-carboxaldehyde

Ethyl 2-methyloxaxoline-4-carboxylate was prepared according to the published procedure (*Heterocycles* 1976, 4, 1688).

To an ambient temperature solution of ethyl 2-methyloxaxoline-4-carboxylate (6.28 g, 40 mmol) in benzene (300 mL) was added copper (I) bromide (6.31 g, 44 mmol) and then copper (II) acetate (7.99 g, 44 mmol). To this mixture was added tertiary butyl perbenzoate (11.4 mL, 60 mmol) dropwise over 15 min and the reaction warmed slightly to the touch. The black mixture was refluxed 24 h, cooled to ambient temperature and filtered through a celite pad (ether rinse). The filtrate was washed with aqueous ammonium chloride, water and brine, then it was dried over sodium sulfate and concentrated. The tan residue was purified by flash chromatography on silica gel (80 g) eluting with 40% ethyl acetate/hexane. After a 100 mL forerun, 20 mL fractions were collected. Fractions 11–22 were collected and concentrated to afford 4.27 g (69%) of ethyl 2-methyloxazole-4-carboxylate as a yellow oil which had: NMR d 8.04 (s, 1H), 4.32 (q, J=7 Hz, 2H), 2.46 (s, 3H), 1.33 (t, J=7 Hz, 3H). This material was used without further purification.

A solution of ethyl 2-methyloxazole-4-carboxylate (0.31 g, 2.0 mmol) in tetrahydrofuran (5 mL) was chilled to −65°

C. and diisobutylaluminum hydride (4.1 mL of a 1 N solution in toluene, 4.1 mmol) was added dropwise over 15 min. The solution was allowed to warm to ambient temperature and stir 15 min. The reaction was chilled to 5° C. and carefully quenched by addition of methanol (2 mL). The reaction mixture was returned to ambient temperature and water (0.18 mL) was added followed by sodium fluoride 1.68 g). This mixture was stirred 30 min, then dried with magnesium sulfate and filtered. The filtrate was concentrated and azeotroped with chloroform to afford 0.215 g (96%) of 4-hydroxymethyl-2-methyloxazole as a pale oil which had: NMR δ 7.45 (s, 1H), 4.52 (d, J=6 Hz, 2H), 3.41 (br s, 1H), 2.42 (s, 3H).

A solution of 4-hydroxymethyl-2-methyloxazole (0.79 g, 6.99 mmol) in methylene chloride (25 mL) was treated with Dess-Martin reagent (8.9 g, 20.97 mmol) and stirred 24 h. The reaction was quenched by addition of saturated aqueous sodium thiosulfate and stirred 30 min. The mixture was filtered. The filtrate was repeatedly extracted with methylene chloride. The combined organic layer was washed with saturated aqueous bicarbonate (twice), water and brine. The organic phase was dried over sodium sulfate and concentrated to a oily white solid. This residue was triturated with ether and filtered. The filtrate was concentrated to afford 0.541 g (69%) of 2-methyloxazole-4-carboxaldehyde as a light yellow solid which had: NMR d 9.88 (s, 1H), 8.15 (s, 1H), 2.52 (s, 3H).

PREPARATION 29

The compounds in table 1 were made by essentially the same procedures as exemplified by Preparation 28.

| Prep | IUPAC Name | NMR |
|---|---|---|
| 29 | 3-(2-Chloro-pyridin-3-yl)-6-fluoro-2-[2-(2-hydroxy-phenyl)-vinyl]-3H-quinazolin-4-one | ($CDCl_3$+DMSO -d6) δ5.99 (1H, d, J=15), 6.16–6.24 (1H, m), 6.38(1H, d, J=10), 6.42–6.66(2H, m), 6.93–7.12(2H, m), 7.23–7.45 (3H, m), 7.60(1H, d, J=15), 8.04(1H, m), 9.23(1H, broad s). |
| 30 | 2{2-[6-Fluoro-3-(2-methyl-pyridin-3-yl)-4-oxo-3,4-dihydro-quinazolin-2-yl]-vinyl}-4-methyl-benzonitrile | ($CDCl_3$+DMSO-d6) δ2.03 (3H, s), 2.07(3H, s), 6.15 (1H, d, J=15), 6.82–6.94 (2H, m), 7.11–7.60(7H, m), 7.91(1H, d, J=15), 8.41 (1H, m). |
| 31 | 2-[2-(5-Diethylaminomethyl-2-fluoro-phenyl)-vinyl]-6-fluoro-3-(2-methyl-pyridin-3-yl)-3H-quinazolin-4-one | ($CDCl_3$+DMSO-d6) δ1.72 (6H, broadened t), 2.76 (3H, s), 2.67(2H, broad q), 3.05(2H, broad q), 3.96 (2H, m), 6.40(d, J=15), 6.69–6.78(1H, m), 7.13–7.31(2H, m), 7.48–7.58 (2H, m), 7.72–7.80(1H, m), 7.88(1H, d, J=15), 8.05–8.16(2H, m), 8.44 (1H, m). |
| 32 | 6-Fluoro-2-[2-(2-fluoro-5-pyrrolidin-1-ylmethyl-phenyl)-vinyl]-3-(2-methyl-pyridin-3-yl)-3H-quinazolin-4-one | ($CDCl_3$+DMSO-d6) δ1.72 (4H, broadened s), 2.38 (3H, s), 2.64(2H, m), 3.07 (2H, m), 3.95(2H, m), 6.40 (1H, d, J=15), 6.71–6.80 (2H, m), 7.15–7.32(2H, m), 7.49–7.59 (3H, m), 7.74–7.82(2H, m), 7.90 (1H, d, J=15), 8.07–8.17 (2H, m), 8.47(1H, m). |

-continued

| Prep | IUPAC Name | NMR |
|---|---|---|
| 33 | 6-Fluoro-2-[2-(2-fluoro-5-pyrrolidin-1-ylmethyl-phenyl)-vinyl]-3-(2-methyl-pyridin-3-yl)-3H-quinazolin-4-one | ($CDCl_3$+DMSO-d6) δ1.72 (6H, broadened t), 2.76 (3H, s), 2.67(2H, broad q), 3.05(2H, broad q), 3.96 (2H, m), 6.40(d, J=15), 6.69–6.78(1H, m), 7.13–7.31(2H, m), 7.48–7.58 (2H, m), 7.72–7.80(1H, m), 7.88(1H, d, J=15), 8.05–8.16(2H, m), 8.44 (1H, m). |

PREPARATION 34

6-Fluoro-3-(2-methyl-pyridin-3-yl)-2-[2-(2-methyl-thiazol-4-yl)-ethyl]-3H-quinazolin-4-one To a slurry of 10% palladium on carbon (0.15 g) in methanol(12 mL) were added 6-fluoro-3-(2-methyl-pyridin-3-yl)-2-[2-(2-methyl-thiazol-4-yl)-vinyl]-3 H-quinazolin-4-one (0.075 g, 0.198 mmol) and ammonium formate (1.2 g, 19 mmol). The mixture was refluxed overnight, cooled and filtered through celite. The pad was washed with methanol. The filtrate was concentrated. The residue was partitioned between chloroform and water. The phases were separated and the aqueous layer was extracted with chloroform. The combined organic phase was washed with water and brine, dried over magnesium sulfate, and concentrated to afford 0.035 g (47%) of 6-fluoro-3-(2-methyl-pyridin-3-yl)-2-[2-(2-methyl-thiazol-4-yl)-ethyl]-3H-quinazolin-4-one as a white solid.

Melting point 151–153° C.; NMR δ 8.62 (dd, J=1.5, 5 Hz, 1h), 7.86 (dd, J=3, 8.5 Hz, 1H), 7.73 (dd, J=5, 9 Hz, 1H), 7.49 (dt, J=3, 8 Hz, 1h), 7.41 (dd, J=1.5, 8 Hz, 1H), 7.30 (dd, J=5, 8Hz, 1H), 6.70(s,1H), 3.19 (sym m, 2H), 2.67 (m, 2H), 2.59 (s, 3H), 2.28 (s, 3H).

What is claimed is:

1. An atropisomer of the formula

Ia

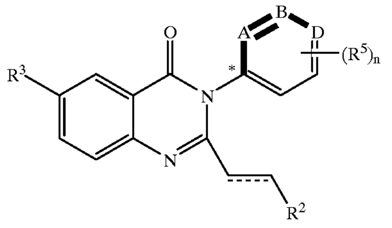

wherein each of “A, B and D” is nitrogen or —CH—, with the proviso that only one of “A”, “B” and “D” can be nitrogen; wherein n is an integer from one to four and wherein each $R^5$ is a substituent on any carbon atom of the “A, B, D” ring capable of supporting an additional bond, with the proviso that one $R^5$ must be attached to a carbon atom ortho to the asterisked carbon of the ring; wherein each $R^5$ may be independently selected from the group consisting of $(C_1–C_6)$alkyl and halogen;

$R^2$ is a phenyl group of the formula:

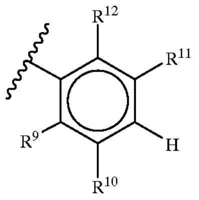

$R^3$ is hydrogen or halo;

$R^9$ is hydrogen, halo, $CF_3$, $(C_1-C_6)$alkyl optionally substituted with one to three halogen atoms, $(C_1-C_6)$ alkoxy optionally substituted with one to three halogen atoms, $(C_1-C_6)$alkylthiol, amino-$(CH_2)_s$—, $(C_1-C_6)$ alkyl-NH—$(CH_2)_s$—, di$(C_1-C_6)$alkyl-N—$(CH_2)_s$—, $(C_3-C_7)$cycloalkyl-NH—$(CH_2)_s$—, $H_2N$—(C═O)—$(CH_2)_s$—, $(C_1-C_6)$alkyl-HN—(C═O)—$(CH_2)_s$—, di$(C_1-C_6)$alkyl-N—(C═O)—$(CH_2)_s$—, $(C_3-C_7)$ cycloalkyl-NH—(C═O)—$(CH_2)_s$—, $R^{13}$O—$(CH_2)_s$—, $R^{13}$O—(C═O)—$(CH_2)_s$—, H(O═C)—NH—$(CH_2)_s$—, $(C_1-C_6)$alkyl-(O═C)—NH—$(CH_2)_s$—,

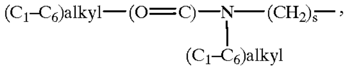

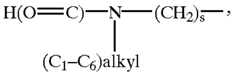

H—(C═O)—$(CH_2)_s$—, $(C_1-C_6)$alkyl-(C═O)—, hydroxy, hydroxy-$(C_1-C_6)$alkyl-, $(C_1-C_6)$alkyl-O—$(C_1-C_6)$alkyl-, or —CN;

$R^{10}$ is hydrogen or halo;

$R^{11}$ is selected from hydrogen, halo, $CF_3$, $(C_1-C_6)$alkyl optionally substituted with one to three halogen atoms, $(C_1-C_6)$alkoxy optionally substituted with one to three halogen atoms, $(C_1-C_6)$alkylthiol, amino-$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, amino-$(C_1-C_6)$alkyl-NH—$(CH_2)_p$—, $(C_1-C_6)$alkyl-NH—$(C_1-C_6)$alkyl-NH—$(CH_2)_p$—, di$(C_1-C_6)$alkyl-N-$(C_1-C_6)$alkyl-NH—$(CH_2)_p$—,

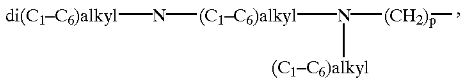

$H_2N$—(C═O)—$(CH_{2p}$—, $(C_1-C_6)$alkyl-HN—(C═O)—$(CH_2)_p$—, di$(C_1-C_6)$alkyl-N—(C═O)—$(CH_2)_p$, $(C_3-C_7)$cycloalkyl-NH—(C═O)—$(CH_2)_p$—, $R^{13}$O—$(CH_2)_p$—, $R^{13}$O—(C═O)—$(CH_2)_p$—, H(O═C)—O—, H(O═C)—O—$(C_1-C_6)$alkyl-, H(O═C)—NH—$(CH_2)_p$—, $(C_1-C_6)$alkyl-(O═C)—NH—$(CH_2)_p$—, —CHO, H—(C═O)—$(CH_2)_p$—, $(C_1-C_6)$alkyl-(C═O)—$(CH_2)_p$—,

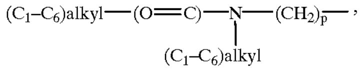

-continued

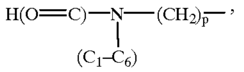

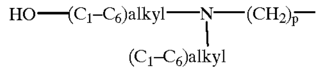

$(C_1-C_6)$alkyl-(C═O)—O—$(CH_2)_p$—, amino-$(C_1-C_6)$ alkyl-(C═O)—O—$(CH_2)_p$—, $(C_1-C_6)$alkyl-(C═)—O—$(CH_2)_p$—, amino-$(C_1-C_6)$alkyl-(C═O)—O—$(CH_2)_p$—, $(C_1-C_6)$alkyl-(C═O)—O—$(CH_2)_p$—, $(C_1-C_6)$alkyl-NH—$(C_1-C_6)$alkyl-(C═O)—O—$(CH_2)_p$—, di$(C_1-C_6)$alkyl-N—$(C_1-C_6)$alkyl-(C═O)—O—$(CH_2)_p$—, amino-$(C_1-C_6)$alkyl-O—(C═O)— $(CH_2)_p$—, $(C_1-C_6)$alkyl-NH—$(C_1-C_6)$ alkyl-O—(C═O)—$(CH_2)_p$—, di$(C_1-C_6)$alkyl-N—$(C_1-C_6)$alkyl-O—(C═O)—$(CH_2)_p$—, hydroxy, hydroxy-$(C_1-C_6)$alkyl-, hydroxy-$(C_1-C_6)$alkyl-NH—$(CH_2)_p$—, $(C_1-C_6)$alkyl-O—$(C_1-C_6)$alkyl-, —CN, piperidine-$(CH_2)_p$—, pyrrolidine-$(CH_2)_p$—, and 3-pyrroline-$(CH_2)_p$—, wherein said piperidine, pyrrolidine and 3-pyrroline moieties of said piperidine-$(CH_2)_p$—, pyrrolidine-$(CH_2)_p$— and 3-pyrroline-$(CH_2)_p$— groups may optionally be substituted on any of the ring carbon atoms capable of supporting an additional bond, with zero to two substituents, with a substituent independently selected from halo, $CF_3$, $(C_1-C_6)$alkyl optionally substituted with one to three halogen atoms, $(C_1-C_6)$alkoxy optionally substituted with one to three halogen atoms, $(C_1-C_6)$alkylthiol, amino-$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH?)_p$—, amino-$(C_1-C_6)$alkyl-NH—$(CH_2)_p$—, $(C_1-C_6)$alkyl-NH—$(C_1-C_6)$alkyl-NH-$CH_2)_p$—, di$(C_1-C_6)$alkyl-N—$(C_1-C_6)$alkyl-NH—$(CH_2)_p$—, $(C_1-C_6)$alkyl—O—$(C_1-C_6)$alkyl-,

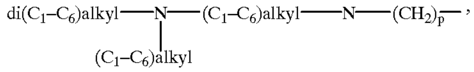

$H_2N$(C═O)—$(CH_2)_p$—, $(C_1-C_6)$alkyl-HN—(C═O)—$(CH_2)_p$—, di$(C_1-C_6)$alkyl-N—(C═O)—$(CH_2)_p$, $(C_3-C_7)$cycloalkyl-NH—(C═O)—$(CH_2)_p$—, $R^{13}$O—$(CH_2)_p$—, $R^{13}$)—(C═O)—$(CH_2)_p$—, H(O═C)—O—, H(O═C)—O—$(C_1-C_6)$alkyl-, H(O═C)—NH—$(CH_2)_p$—, $(C_1-C_6)$alkyl-(O═)NH—$(CH_2)_p$—, —CHO, H—(C═O)—$(CH_2)_p$—, $(C_1-C_6)$ alkyl-(C═O)—,

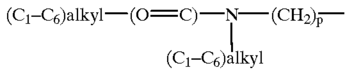

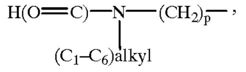

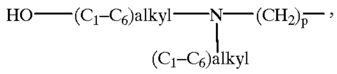

$(C_1-C_6)$alkyl-(C═O)—O—NH—$(CH_2)_p$—, amino-$(C_1-C_6)$alkyl-(C═O)—O—$(CH_2)_p$—, $(C_1-C_6)$alkyl-NH—$(C_1-C_6)$alkyl-(C═O)—O—$(CH_2)_p$—, di$(C_1-C_6)$alkyl-N—$(C_1-C_6)$alkyl-(C═O)—O—$(CH_2)_p$—, hydroxy, hydroxy-$(C_1-C_6)$alkyl-, hydroxy-$(C_1-C_6)$alkyl-NH—$(CH_2)_p$—, and —CN;

$R^{12}$ is hydrogen, —CN or halo;

each p is independently an integer from zero to 4; and s is an integer from zero to 4;

wherein the dashed bond represents a double bond;

or the pharmaceutically acceptable salts of such compounds.

2. A compound according to claim 1 wherein $R^3$ is hydrogen, halo or $(C_1–C_6)$alkyl.

3. The compound according to claim 1 wherein "B" is nitrogen, "A" and "D" are carbon and $R^3$ is hydrogen.

4. A compound according to claim 1 wherein $R^5$ is chloro or methyl.

5. A compound according to claim 3 wherein n is one and $R^5$ is a substituent ortho to the asterisked carbon.

6. The compound according to claim 1 wherein $R^9$ is fluoro, chloro, —CN or hydroxy; or $R^{11}$ is —CHO, chloro, fluoro, methyl, $(C_1–C_6)$alkyl-NH—$(CH_2)_p$—, di$(C_1–C_6)$alkyl-N—$(CH_2)_p$—, or cyano.

7. The compound according to claim 2 wherein $R^9$ is fluoro, chloro, —CN or hydroxy; or $R^{11}$ is —CHO, chloro, fluoro, methyl, $(C_1–C_6)$alkyl-NH—$(CH_2)_p$—, di$(C_1–C_6)$alkyl-N—$(CH_2)_p$—, or cyano.

8. A compound according to claim 1 wherein $R^2$ is heteroaryl and said heteroaryl is either an six-membered heterocycle wherein "K", "L" and "M" are carbon, or "K" and "L" are carbon and "M" is nitrogen, or said heteroaryl is an five membered heterocycle wherein "T" is nitrogen, "P" is sulfur and "Q" is carbon, or "T" is nitrogen or sulfur, "Q" is nitrogen or sulfur and "P" is carbon or "T" is oxygen and "P" and "Q" are each carbon.

9. The compound according to claim 1 wherein said compound is selected from the group consisting of:

(S)-6-fluoro-2-[2-(2-fluoro-phenyl)-vinyl-3-(2-methyl-pyridin-3-yl)-3H-quinazolin-4-one;

(S)-2-{2-[6-fluoro-3-(2-methyl-pyridin-3-yl)-4-oxo-3,4-dihydro-quinazolin-2-yl]-vinyl}-benzonitrile;

(S)-2-{2-[6-fluoro-3-(2-methylpyridin-3-yl)-4-oxo-3,4-dihydroquinazolin-2-yl]-vinyl}-benzonitrile;

(S)-2-{(2-chloro-pyridin-3-yl)-6-fluoro-4-oxo-3,4-dihydroquinazol-in-2-yl]-vinyl}-benzonitrile;

(S)-2-{2-[6-fluoro-3-(2-methyl-pyridin-3-yl)-4-oxo-3,4-dihydro-quinazolin-2yl]-vinyl}-4-methyl-benzonitrile;

(S)-2-[2-(5-diethylaminomethyl-2-fluoro-phenyl)-vinyl]-6-fluoro-3-(2-methyl-pyridin-3-yl)-3H-quinazolin-4-one, or (S)-6-fluoro-2-[2-(2-fluoro-5-pyrrolidin-1-ylmethyl-phenyl)-vinyl]-3-(2-methyl-pyridin-3-yl)-3H-quinazolin-4-one.

10. A pharmaceutical composition for treating a condition selected from epilepsy and convulsions, in a mammal, comprising an amount of a compound according to claim 1 effective in treating such condition and a pharmaceutically acceptable carrier.

11. A method for treating a condition selected from epilepsy and convulsions, in a mammal, comprising administering to a mammal requiring such treatment an amount of a compound according to claim 1 effective in treating such condition.

12. A pharmaceutical composition for treating a condition selected from epilepsy and convulsions, in a mammal, comprising an AMPA receptor antagonizing effective amount compound according to claim 1 and a pharmaceutically acceptable carrier.

13. A method for treating a condition selected from epilepsy and convulsions, in a mammal, comprising administering to a mammal requiring such treatment an AMPA receptor antagonizing effective amount of a compound according to claim 1.

* * * * *